(12) United States Patent
Hirose et al.

(10) Patent No.: US 9,381,174 B2
(45) Date of Patent: Jul. 5, 2016

(54) COMPOSITION AND METHOD FOR EXTERMINATING ANIMAL PARASITE

(71) Applicant: Mitsui Chemicals Agro, Inc., Tokyo (JP)

(72) Inventors: Mai Hirose, Tokyo (JP); Michikazu Nomura, Mobara (JP); Kunio Okumura, Mobara (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 0 days.

(21) Appl. No.: 14/438,513

(22) PCT Filed: Nov. 5, 2013

(86) PCT No.: PCT/JP2013/079948
§ 371 (c)(1),
(2) Date: Apr. 24, 2015

(87) PCT Pub. No.: WO2014/069665
PCT Pub. Date: May 8, 2014

(65) Prior Publication Data
US 2015/0297541 A1 Oct. 22, 2015

(30) Foreign Application Priority Data
Nov. 5, 2012 (JP) .................. 2012-243601

(51) Int. Cl.
| A61K 31/167 | (2006.01) |
| A01N 37/30 | (2006.01) |
| A01N 47/02 | (2006.01) |
| A01N 37/22 | (2006.01) |

(52) U.S. Cl.
CPC .............. *A61K 31/167* (2013.01); *A01N 37/22* (2013.01); *A01N 37/30* (2013.01); *A01N 47/02* (2013.01)

(58) Field of Classification Search
None
See application file for complete search history.

(56) References Cited

U.S. PATENT DOCUMENTS

2011/0201687 A1  8/2011  Kobayashi et al.
2012/0022263 A1  1/2012  Kinoshita

FOREIGN PATENT DOCUMENTS

| JP | 2005206582 | | 8/2005 |
| WO | 2010018714 | A1 | 2/2010 |
| WO | 2010089881 | A1 | 8/2010 |
| WO | 2010090282 | A1 | 8/2010 |
| WO | 2012020483 | A1 | 2/2012 |
| WO | 2012020484 | A1 | 2/2012 |
| WO | 2012077221 | A1 | 6/2012 |
| WO | 2012164698 | A1 | 12/2012 |

OTHER PUBLICATIONS

International Search Report dated dated Feb. 10, 2014 filed in PCT/JP2013/079948.
Extended European Search Report dated Mar. 8, 2016 issued in the corresponding European patent application No. 13850833.8.

*Primary Examiner* — Brian J Davis
(74) *Attorney, Agent, or Firm* — Rankin, Hill & Clark LLP

(57) ABSTRACT

A composition for exterminating an animal parasite, the composition including, as an active ingredient, at least one of 3-aminoxalylaminobenzamide derivatives represented by the following Formula (1):

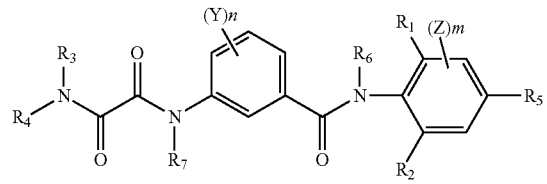

(1)

($R_1$ and $R_2$ represent a halogen atom, a C1-C5 haloalkyl group, a C1-C5 alkyl group, or the like. $R_3$ and $R_4$ represent a C1-C8 alkyl group, a C1-C8 haloalkyl group, or the like. $R_5$ represents a C1-C5 haloalkyl group. $R_6$ and $R_7$ represent a hydrogen atom, a C1-C5 alkyl group, or the like. Y represents a halogen atom or the like. Z represents a halogen atom or the like. n represents 0-4, and m represents 0-2.)

9 Claims, No Drawings

COMPOSITION AND METHOD FOR EXTERMINATING ANIMAL PARASITE

TECHNICAL FIELD

The present invention relates to a composition and a method for exterminating an animal parasite.

BACKGROUND ART

WO 2010/089881, WO 2010/090282, WO 2012/020483, WO 2012/020484, WO 2012/077221, and WO 2012/164698 describe various 3-aminoxalylaminobenzamide derivatives that have agriculturally significant pesticidal activity and methods for using the derivatives. These specifications exemplify specific concentrations that are efficacious against diamondback moths, two-spotted spider mites, and green peach aphids, which are agricultural pests, and the details of the pesticidal effects against these pests.

Examples of known animal parasiticides for administration to an animal to exterminate an animal parasite include formulations of imidacloprid and fipronil. However, some parasites are impossible or difficult to exterminate with these animal parasiticides. There is a continuing need for a novel compound that has animal parasiticidal activity.

SUMMARY OF INVENTION

Problems to be Solved by the Invention

The foregoing International Publications describe that the 3-aminoxalylaminobenzamide derivatives may exterminate an animal parasite, but do not disclose a specific concentration that is efficacious against an animal parasite or details of pesticidal effects against an animal parasite, and do not substantially disclose application of the derivatives as animal parasiticides.

The invention has an object of providing a composition for exterminating an animal parasite, the composition having excellent animal parasiticidal activity, and a method for exterminating an animal parasite.

Means of Solving the Problems

As a result of assiduous research aimed at solving the problems described above, the inventors have found that a compound represented by the following Formula (1) has excellent animal parasiticidal activity, thereby completing the invention.

The invention is as follows:

[1] A composition for exterminating an animal parasite, the composition including, as an active ingredient, a 3-aminoxalylaminobenzamide derivative represented by the following Formula (1):

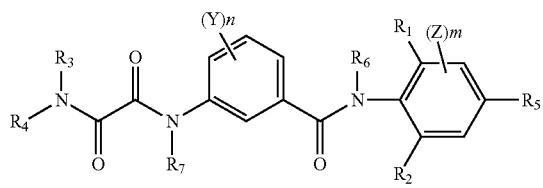

(1)

(In the formula, each of $R_1$ and $R_2$ independently represents a hydrogen atom, a C1-C3 alkoxy group, a C1-C3 haloalkoxy group, a C1-C3 alkylthio group, a C1-C3 alkylsulfinyl group, a C1-C3 alkylsulfonyl group, a C1-C3 haloalkylthio group, a C1-C3 haloalkylsulfinyl group, a C1-C3 haloalkylsulfonyl group, a halogen atom, a C1-C5 haloalkyl group, or a C1-C5 alkyl group.

Each of $R_3$ and $R_4$ independently represents a hydrogen atom, a C1-C8 alkyl group, a C1-C8 haloalkyl group, a C2-C6 alkenyl group, a C2-C6 haloalkenyl group, a C2-C6 alkynyl group, a C3-C8 cycloalkyl group, or a C3-C8 halocycloalkyl group, or $R_3$ and $R_4$ may together form a C3-C8 alkylene group, the C3-C8 alkylene group being optionally substituted by a halogen atom or a C1-C5 alkyl group.

$R_5$ represents a C1-C5 haloalkyl group.

Each of $R_6$ and $R_7$ independently represents a hydrogen atom, a C1-C5 alkyl group, a C3-C8 cycloalkyl group, a C1-C5 haloalkyl group, a C1-C3 alkoxy-C1-C4 alkyl group, a C2-C6 alkenyl group, a C2-C6 haloalkenyl group, a C1-C4 alkylcarbonyl group, a C1-C4 haloalkylcarbonyl group, a C1-C4 alkylsulfonyl group, a C1-C4 haloalkylsulfonyl group, a C1-C3 alkoxycarbonyl group, or a C1-C3 haloalkoxycarbonyl group.

Each Y independently represents a hydrogen atom, a halogen atom, a hydroxyl group, a nitro group, a cyano group, a C1-C5 alkyl group, a C1-C5 haloalkyl group, a C1-C3 alkylamino group, a di-C1-C3 alkylamino group, a C1-C3 alkoxy group, or a C1-C3 haloalkoxy group.

Each Z independently represents a hydrogen atom, a halogen atom, a hydroxyl group, a nitro group, a cyano group, a C1-C5 alkyl group, a C1-C5 haloalkyl group, a C1-C3 alkoxy group, or a C1-C3 haloalkoxy group.

n represents an integer from 0 to 4, and m represents an integer from 0 to 2.)

[2] The composition for exterminating an animal parasite according to [1], in which, in Formula (1), $R_1$ represents a methoxy group, a trifluoromethoxy group, a trifluoromethylthio group, a trifluoromethylsulfinyl group, a trifluoromethylsulfonyl group, a chlorine atom, a bromine atom, an iodine atom, a methyl group, an ethyl group, an isopropyl group, a difluoromethoxy group, or a trifluoromethyl group; $R_2$ represents a chlorine atom, a bromine atom, an iodine atom, a methyl group, or an ethyl group; each of $R_3$ and $R_4$ independently represents a C1-C4 alkyl group, a C1-C4 haloalkyl group, a C3-C4 alkenyl group, a C3-C4 haloalkenyl group, a propargyl group, or a C3-C5 cycloalkyl group, or $R_3$ and $R_4$ together form a C4-C5 alkylene group that is optionally substituted by a methyl group; $R_5$ represents a C3-C4 haloalkyl group; $R_6$ and $R_7$ represent a hydrogen atom; Y represents a hydrogen atom or a halogen atom; and Z represents a hydrogen atom.

[3] The composition for exterminating an animal parasite according to [2], in which the 3-aminoxalylaminobenzamide derivative represented by Formula (1) is represented by any one of the following Formulae (2) to (6):

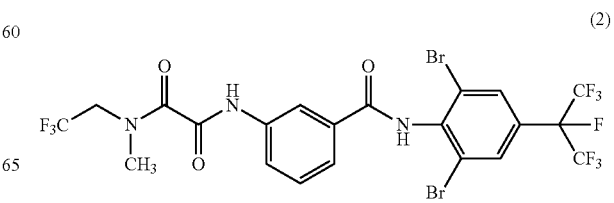

(2)

[4] The composition for exterminating an animal parasite according to [2], in which in Formula (1), $R_1$ represents a trifluoromethyl group, a difluoromethoxy group, a trifluoromethylthio group, a trifluoromethylsulfinyl group, a trifluoromethylsulfonyl group; $R_2$ represents a chlorine atom, a bromine atom, an iodine atom, a methyl group, or an ethyl group; each of $R_3$ and $R_4$ independently represents a C1-C4 alkyl group or a C1-C4 haloalkyl group; $R_5$ represents a C3-C4 haloalkyl group; each of $R_6$ and $R_7$ independently represents a hydrogen atom or a C1-C5 alkyl group; Y represents a fluorine atom; and Z represents a hydrogen atom.

[5] The composition for exterminating an animal parasite according to [4], in which the 3-aminoxalylaminobenzamide derivative represented by Formula (1) is represented by any one of the following Formulae (7) to (26):

(16)
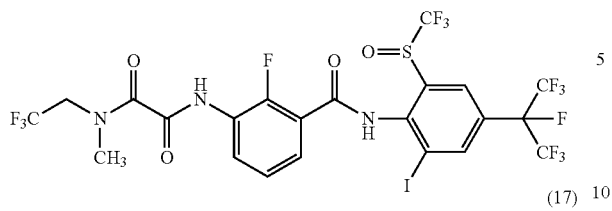

(17)
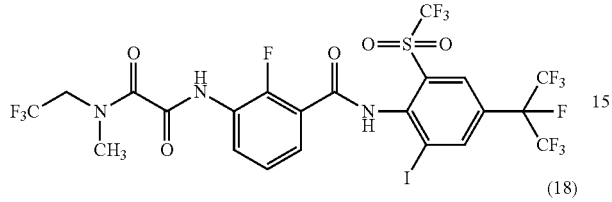

(18)
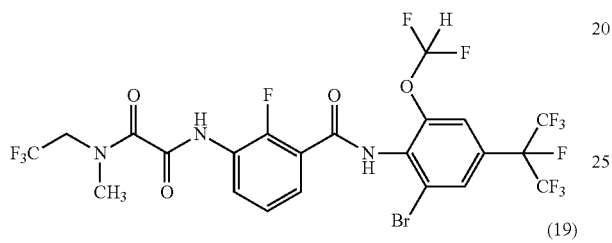

(19)
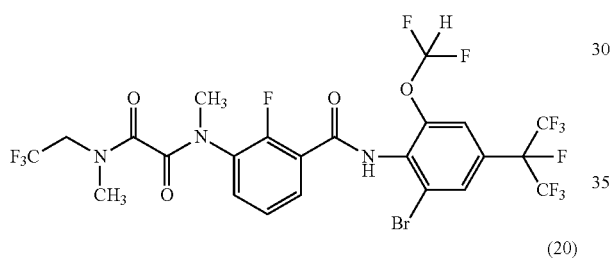

(20)
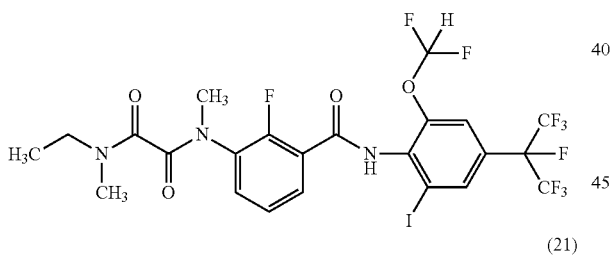

(21)
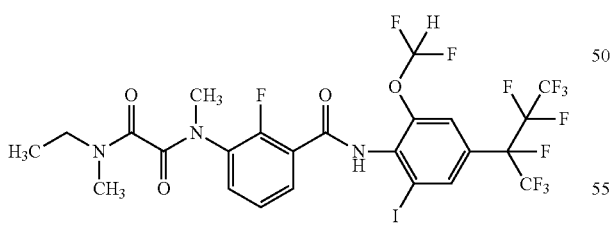

(22)
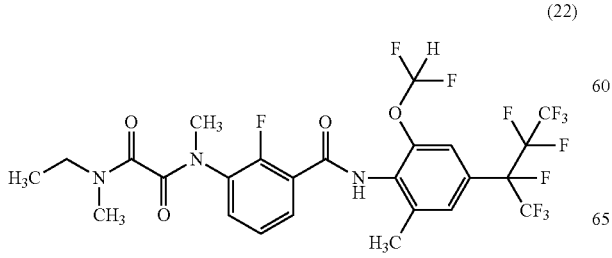

(23)
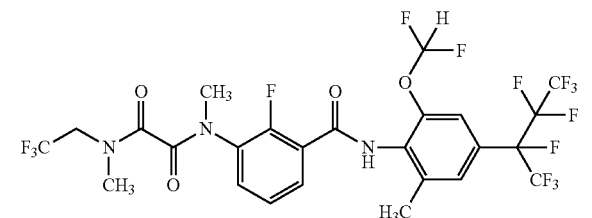

(24)
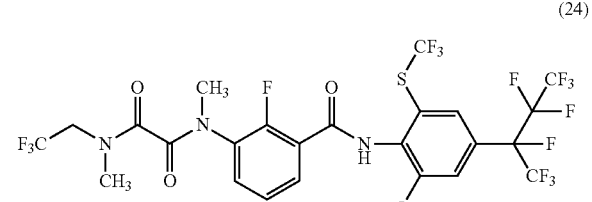

(25)
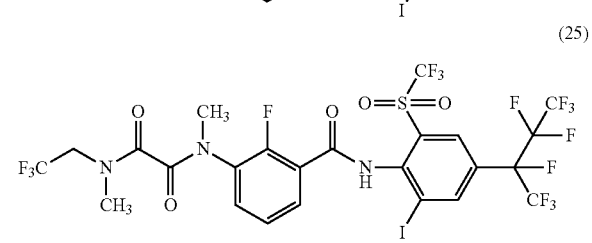

(26)
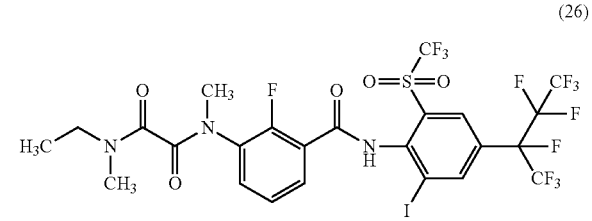

A method for exterminating an animal parasite, the method including administering, to an animal, the composition for exterminating an animal parasite according to any one of [1]-[5].

[7] The method for exterminating an animal parasite according to [6], in which the animal parasite is an ectoparasite.

[8] The method for exterminating an animal parasite according to [7], in which the ectoparasite is a Siphonaptera pest.

[9] The method for exterminating an animal parasite according to [7], in which the ectoparasite is an Acarina pest.

[10] A compound represented by the following Formula (1):

(1)
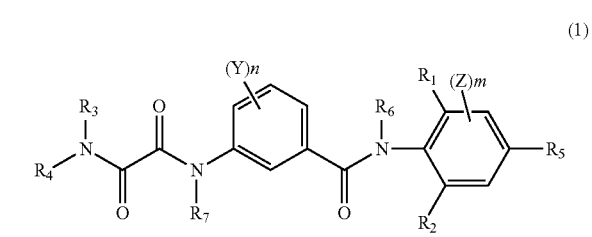

(In the formula, $R_1$ represents a trifluoromethyl group, a difluoromethoxy group, a trifluoromethylthio group, a trifluoromethylsulfinyl group, or a trifluoromethylsulfonyl group, $R_2$ represents a chlorine atom, a bromine atom, an iodine atom, a methyl group, or an ethyl group, each of $R_3$ and $R_4$ independently represents a C1-C4 alkyl group or a C1-C4 haloalkyl group, $R_5$ represents a C3-C4 haloalkyl group, each of $R_6$ and $R_7$ independently represents a hydrogen atom or a C1-C5 alkyl group, Y represents a fluorine atom, Z represents a hydrogen atom, n represents an integer from 0 to 4, and m represents an integer from 0 to 2.)

[11] The compound according to [10], in which the 3-aminoxalylaminobenzamide derivative represented by Formula (1) is represented by any one of the following Formulae (7) to (26):

(7)
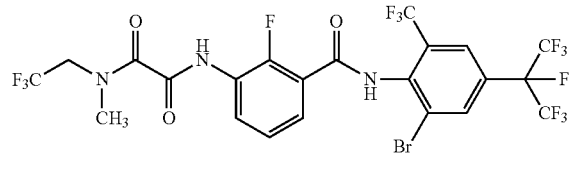

(8)
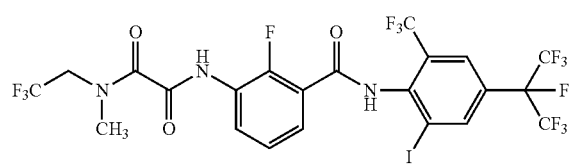

(9)
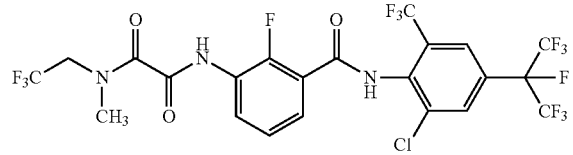

(10)
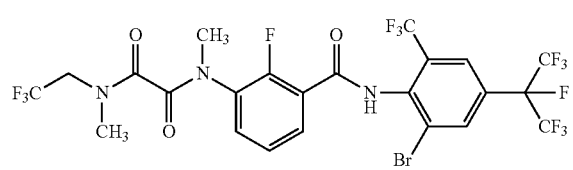

(11)
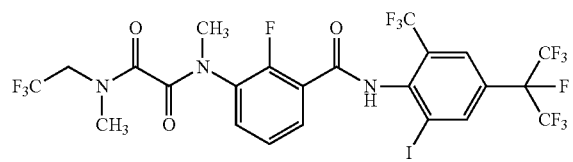

(12)
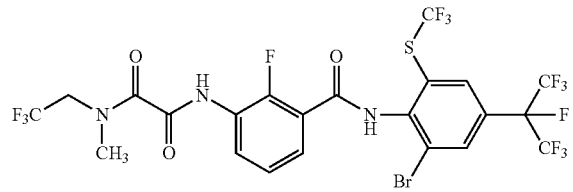

-continued

(13)
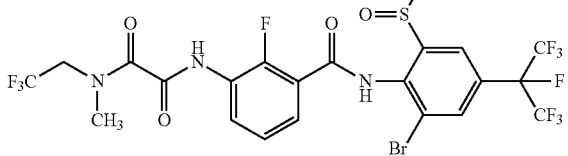

(14)
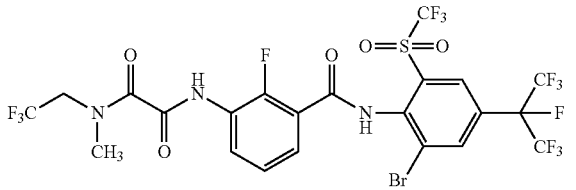

(15)
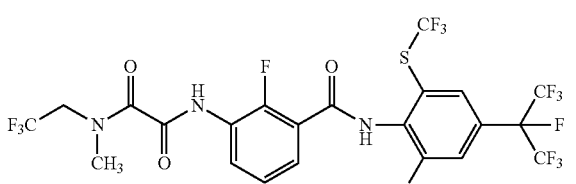

(16)
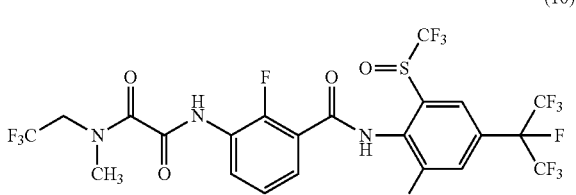

(17)
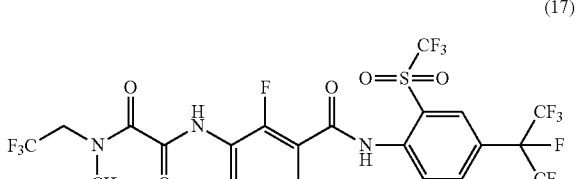

(18)
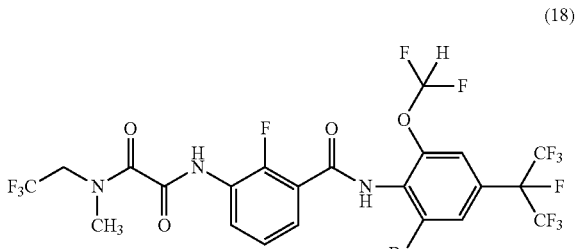

(19)
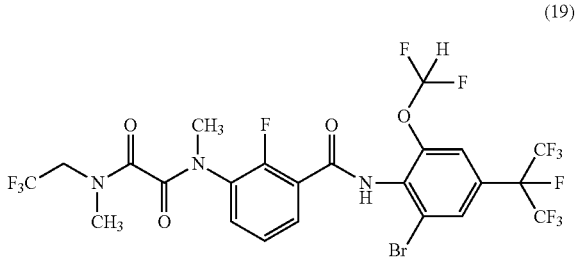

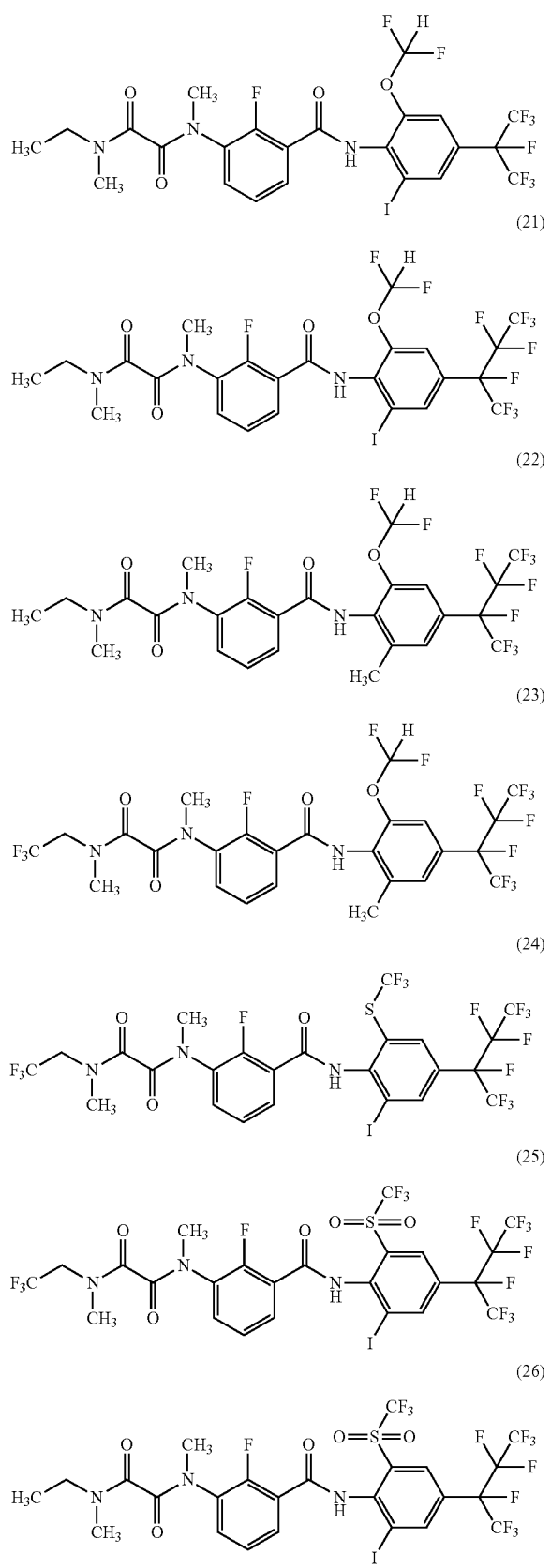

Effects of the Invention

According to the invention, a composition for exterminating an animal parasite, the composition having excellent animal parasiticidal activity, and a method for exterminating an animal parasite, can be provided.

DESCRIPTION OF EMBODIMENTS

The composition for exterminating an animal parasite of the invention includes at least one of 3-aminoxalylaminobenzamide derivatives represented by the following Formula (1).

Such a structure allows for high animal parasiticidal activity in a case in which the composition is applied in animals.

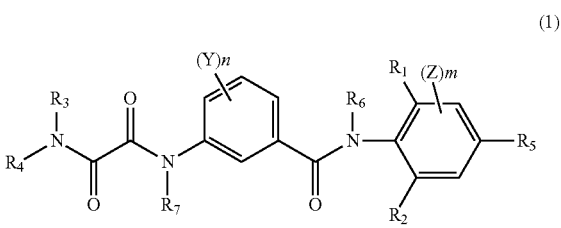

(1)

In Formula (1), each of $R_1$ and $R_2$ independently represents a hydrogen atom, a C1-C3 alkoxy group, a C1-C3 haloalkoxy group, a C1-C3 alkylthio group, a C1-C3 alkylsulfinyl group, a C1-C3 alkylsulfonyl group, a C1-C3 haloalkylthio group, a C1-C3 haloalkylsulfinyl group, a C1-C3 haloalkylsulfonyl group, a halogen atom, a C1-C5 haloalkyl group, or a C1-C5 alkyl group.

Each of $R_3$ and $R_4$ independently represents a hydrogen atom, a C1-C8 alkyl group, a C1-C8 haloalkyl group, a C2-C6 alkenyl group, a C2-C6 haloalkenyl group, a C2-C6 alkynyl group, a C3-C8 cycloalkyl group, or a C3-C8 halocycloalkyl group, or $R_3$ and $R_4$ together form a C3-C8 alkylene group, the C3-C8 alkylene group being optionally substituted by a halogen atom or a C1-C5 alkyl group.

$R_5$ represents a C1-C5 haloalkyl group.

Each of $R_6$ and $R_7$ independently represents a hydrogen atom, a C1-C5 alkyl group, a C3-C8 cycloalkyl group, a C1-C5 haloalkyl group, a C1-C3 alkoxy-C1-C4 alkyl group, a C2-C6 alkenyl group, a C2-C6 haloalkenyl group, a C1-C4 alkylcarbonyl group, a C1-C4 haloalkylcarbonyl group, a C1-C4 alkylsulfonyl group, a C1-C4 haloalkylsulfonyl group, a C1-C3 alkoxycarbonyl group, or a C1-C3 haloalkoxycarbonyl group.

Each Y independently represents a hydrogen atom, a halogen atom, a hydroxyl group, a nitro group, a cyano group, a C1-C5 alkyl group, a C1-C5 haloalkyl group, a C1-C3 alkylamino group, a di-C1-C3 alkylamino group, a C1-C3 alkoxy group, or a C1-C3 haloalkoxy group.

Each Z independently represents a hydrogen atom, a halogen atom, a hydroxyl group, a nitro group, a cyano group, a C1-C5 alkyl group, a C1-C5 haloalkyl group, a C1-C3 alkoxy group, or a C1-C3 haloalkoxy group.

n, which is the degree of substitution in a case in which Y is other than a hydrogen atom, represents an integer from 0 to 4. m, which is the degree of substitution in a case in which Z is other than a hydrogen atom, represents an integer from 0 to 2.

Each of the terms used with respect to general formulae such as Formula (1) according to the invention has the meaning described below.

"Halogen atom" refers to a fluorine atom, a chlorine atom, a bromine atom, or an iodine atom.

With respect to "Ca-Cb (in which a and b represent an integer of 1 or more)", for example, "C1-C3" means that the group contains from 1 to 3 carbon atoms, "C2-C6" means that the group contains from 2 to 6 carbon atoms, and "C1-C4" means that the group contains from 1 to 4 carbon atoms.

"n-" means normal, and "t-" means tertiary.

In the invention, "C1-C3 alkoxy group" refers to a linear or branched alkoxy group that contains from 1 to 3 carbon atoms, such as methoxy, ethoxy, n-propyloxy, and isopropyloxy.

"C1-C3 haloalkoxy group" refers to a linear or branched alkyloxy group that contains from 1 to 3 carbon atoms and that is substituted by one or more halogen atoms, which may be the same or different, such as difluoromethoxy, trifluoromethoxy, pentafluoroethoxy, 1,1,2,2-tetrafluoroethoxy, 2,2,2-trifluoroethoxy, heptafluoro-n-propyloxy, heptafluoroisopropyloxy, and 1,1,2,3,3,3-hexafluoro-n-propyloxy.

"C1-C3 alkylthio group" refers to a linear or branched alkylthio group that contains from 1 to 3 carbon atoms, such as methylthio, ethylthio, n-propylthio, and isopropylthio.

"C1-C3 alkylsulfinyl group" refers to a linear or branched alkylsulfinyl group that contains from 1 to 3 carbon atoms, such as methylsulfinyl, ethylsulfinyl, n-propylsulfinyl, and isopropylsulfinyl.

"C1-C3 alkylsulfonyl group" refers to a linear or branched alkylsulfonyl group that contains from 1 to 3 carbon atoms, such as methylsulfonyl, ethylsulfonyl, n-propylsulfonyl, and isopropylsulfonyl.

"C1-C3 haloalkylthio group" refers to a linear or branched alkylthio group that contains from 1 to 3 carbon atoms and that is substituted by one or more halogen atoms, which may be the same or different, such as difluoromethylthio, trifluoromethylthio, pentafluoroethylthio, 1,1,2,2-tetrafluoroethylthio, 2,2,2-trifluoroethylthio, heptafluoro-n-propylthio, heptafluoroisopropylthio, and 1,1,2,3,3,3-hexafluoro-n-propylthio.

"C1-C3 haloalkylsulfinyl group" refers to a linear or branched alkylsulfinyl group that contains from 1 to 3 carbon atoms and that is substituted by one or more halogen atoms, which may be the same or different, such as difluoromethylsulfinyl, trifluoromethylsulfinyl, pentafluoroethylsulfinyl, 1,1,2,2-tetrafluoroethylsulfinyl, 2,2,2-trifluoroethylsulfinyl, heptafluoro-n-propylsulfinyl, heptafluoroisopropylsulfinyl, and 1,1,2,3,3,3-hexafluoro-n-propylsulfinyl.

"C1-C3 haloalkylsulfonyl group" refers to a linear or branched alkylsulfonyl group that contains from 1 to 3 carbon atoms and that is substituted by one or more halogen atoms, which may be the same or different, such as difluoromethylsulfonyl, trifluoromethylsulfonyl, pentafluoroethylsulfonyl, 1,1,2,2-tetrafluoroethylsulfonyl, 2,2,2-trifluoroethylsulfonyl, heptafluoro-n-propylsulfonyl, heptafluoroisopropylsulfonyl, and 1,1,2,3,3,3-hexafluoro-n-propylsulfonyl.

"C1-C5 alkyl group" refers to a linear or branched alkyl group that contains from 1 to 5 carbon atoms, such as methyl, ethyl, n-propyl, isopropyl, n-butyl, 2-butyl, isobutyl, t-butyl, n-pentyl, isopentyl, 2-pentyl, neopentyl, and t-pentyl.

"C1-C5 haloalkyl group" refers to a linear or branched alkyl group that contains from 1 to 5 carbon atoms and that is substituted by one or more halogen atoms, which may be the same or different, such as monofluoromethyl, difluoromethyl, trifluoromethyl, monochloromethyl, dichloromethyl, trichloromethyl, monobromomethyl, dibromomethyl, tribromomethyl, 1-fluoroethyl, 2-fluoroethyl, 2,2-difluoroethyl, 2,2,2-trifluoroethyl, 2-chloro-2,2-difluoroethyl, 1-chloroethyl, 2-chloroethyl, 2,2-dichloroethyl, 2,2,2-trichloroethyl, 1-bromoethyl, 2-bromoethyl, 2,2-dibromoethyl, 2,2,2-tribromoethyl, 2-iodoethyl, pentafluoroethyl, heptafluoro-n-propyl, heptafluoro-i-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 2,3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, 3,3,4,4,4-pentafluoro-2-butyl, nonafluoro-n-butyl, nonafluoro-2-butyl, 5,5,5-trifluoro-n-pentyl, 4,4,5,5,5-pentafluoro-2-pentyl, 3-chloro-n-pentyl, and 4-bromo-2-pentyl.

"C1-C8 alkyl group" refers to a linear or branched alkyl group that contains from 1 to 8 carbon atoms, such as methyl, ethyl, n-propyl, isopropyl, n-butyl, 2-butyl, isobutyl, t-butyl, n-pentyl, isopentyl, 2-pentyl, neopentyl, t-pentyl, n-hexyl, t-octyl, and n-octyl.

"C1-C8 haloalkyl group" refers to a linear or branched alkyl group that contains from 1 to 8 carbon atoms and that is substituted by one or more halogen atoms, which may be the same or different, such as a monofluoromethyl group, a difluoromethyl group, a trifluoromethyl group, a monochloromethyl group, a dichloromethyl group, a trichloromethyl group, a monobromomethyl group, a dibromomethyl group, a tribromomethyl group, a 1-fluoroethyl group, a 2-fluoroethyl group, a 2,2-difluoroethyl group, a 2,2,2-trifluoroethyl group, a 2-chloro-2,2-difluoroethyl group, a 1-chloroethyl group, a 2-chloroethyl group, a 2,2-dichloroethyl group, a 2,2,2-trichloroethyl group, a 1-bromoethyl group, a 2-bromoethyl group, a 2,2-dibromoethyl group, a 2,2,2-tribromoethyl group, a 2-iodoethyl group, a pentafluoroethyl group, a 2-chloro-1,1,2,2-tetrafluoroethyl group, a 2-bromo-1,1,2,2-tetrafluoroethyl group, a 2-iodo-1,1,2,2-tetrafluoroethyl group, a 3-fluoropropyl group, a 3-chloropropyl group, a 3-bromopropyl group, a 1,3-difluoro-2-propyl group, a 3,3-difluoropropyl group, a 3,3,3-trifluoropropyl group, a 3,3,3-trichloropropyl group, a 1,3-dichloro-2-propyl group, a 1,1,1-trifluoro-2-propyl group, a 1-chloro-3-fluoro-2-propyl group, a 1,1,1,3,3,3-hexafluoro-2-propyl group, a 1,1,1,3,3,3-hexafluoro-2-chloro-2-propyl group, a 2-bromo-1,1,1,3,3,3-hexafluoro-2-propyl group, a 2,2,3,3,3-pentafluoropropyl group, a heptafluoroisopropyl group, a heptafluoro-n-propyl group, a 1-chloro-1,1,2,3,3,3-hexafluoro-2-propyl group, a 1-bromo-1,1,2,3,3,3-hexafluoro-2-propyl group, a 2-chloro-1,1,2,3,3,3-hexafluoro-n-propyl group, a 2-bromo-1,1,2,3,3,3-hexafluoro-n-propyl group, a 4-fluorobutyl group, a 4,4,4-trifluorobutyl group, a nonafluoro-n-butyl group, a nonafluoro-2-butyl group, a 4,4,5,5,5-pentafluoropentyl group, a 3,3,4,4,5,5,5-heptafluoropentyl group, an undecafluoro-2-pentyl group, an undecafluoro-3-pentyl group, an undecafluoro-n-pentyl group, a 6,6,6-trifluorohexyl group, and a 1H,1H-pentadecafluorooctyl group.

"C2-C6 alkenyl group" refers to an alkenyl group that contains from 2 to 6 carbon atoms, which has a double bond in the carbon chain, such as vinyl, allyl, 1-methyl-2-propenyl, 2-methyl-2-propenyl, 2-butenyl, and 3-butenyl.

"C2-C6 haloalkenyl group" refers to a linear or branched alkenyl group, which has a double bond in the carbon chain, the group containing from 2 to 6 carbon atoms and being substituted by one or more halogen atoms, which may be the same or different, such as 2-chloro-2-propenyl, 3-chloro-2-propenyl, 2-bromo-2-propenyl, 3-bromo-2-propenyl, 3,3-difluoro-2-propenyl, 3,3-dichloro-2-propenyl, 3,3-dibromo-2-propenyl, 2,3-dibromo-2-propenyl, 4,4-difluoro-3-butenyl, and 3,4,4-tribromo-3-butenyl.

"C2-C6 alkynyl group" refers to an alkynyl group, which has a triple bond in the carbon chain, the group containing from 2 to 6 carbon atoms, such as propargyl, a 1-methylpropargyl group, 1-butyn-3-yl, and 1-butyn-3-methyl-3-yl.

"C3-C8 cycloalkyl group" refers to a cycloalkyl group, which has a cyclic structure, the group containing from 3 to 8 carbon atoms, such as cyclopropyl, cyclobutyl, cyclopentyl, 2-methylcyclopentyl, 3-methylcyclopentyl, cyclohexyl, 2-methylcyclohexyl, 3-methylcyclohexyl, and 4-methylcyclohexyl.

"C3-C8 halocycloalkyl group" refers to a cycloalkyl group, which has a cyclic structure, the group containing from 3 to 8 carbon atoms and being substituted by one or more halogen atoms, which may be the same or different, such as 2-fluorocyclopropyl, 2,2-difluorocyclopropyl, 2,2,3,3-tetrafluorocyclobutyl, 3,3-difluorocyclobutyl, 2-chlorocyclohexyl, and 4-chlorocyclohexyl.

"C1-C3 alkoxy-C1-C4 alkyl group" refers to a C1-C4 alkyl group that is substituted with a C1-C3 alkoxy group, such as methoxymethyl, ethoxymethyl, and 2-methoxyethyl.

"C1-C4 alkylcarbonyl group" refers to an alkylcarbonyl group that has a linear, branched, or cyclic alkyl group that contains from 1 to 4 carbon atoms, such as acetyl, propionyl, i-propylcarbonyl, cyclopropylcarbonyl, n-butylcarbonyl, 2-butylcarbonyl, and t-butylcarbonyl.

"C1-C4 haloalkylcarbonyl group" refers to an alkylcarbonyl group that has a linear, branched, or cyclic alkyl group that contains from 1 to 4 carbon atoms and that is substituted by one or more halogen atoms, which may be the same or different, such as trifluoroacetyl, pentafluoropropionyl, 2-chloropropionyl, 2,2,2-trifluoropropionyl, heptafluoro-n-propylcarbonyl, heptafluoroisopropylcarbonyl, 1,1,1,3,3,3-hexafluoro-2-propylcarbonyl, 3-fluoro-n-propylcarbonyl, 1-chlorocyclopropylcarbonyl, 2-bromocyclopropylcarbonyl, 3,3,4,4,4-pentafluoro-2-butylcarbonyl, nonafluoro-n-butylcarbonyl, nonafluoro-2-butylcarbonyl, 4-chlorobutylcarbonyl, and 2-iodo-n-propylcarbonyl.

"C1-C4 alkylsulfonyl group" refers to a linear, branched, or cyclic alkylsulfonyl group that contains from 1 to 4 carbon atoms, such as methylsulfonyl, ethylsulfonyl, n-propylsulfonyl, isopropylsulfonyl, cyclopropylsulfonyl, n-butylsulfonyl, 2-butylsulfonyl, isobutylsulfonyl, and t-butylsulfonyl.

"C1-C4 haloalkylsulfonyl group" refers to a linear, branched, or cyclic alkylsulfonyl group that contains from 1 to 4 carbon atoms and that is substituted by one or more halogen atoms, which may be the same or different, such as trifluoromethylsulfonyl, pentafluoroethylsulfonyl, 2-chloroethylsulfonyl, 2,2,2-trifluoroethylsulfonyl, heptafluoro-n-propylsulfonyl, heptafluoroisopropylsulfonyl, 1,1,1,3,3,3-hexafluoro-2-propylsulfonyl, 3-fluoro-n-propylsulfonyl, 1-chlorocyclopropylsulfonyl, 2-bromocyclopropylsulfonyl, 3,3,4,4,4-pentafluoro-2-butylsulfonyl, nonafluoro-n-butylsulfonyl, nonafluoro-2-butylsulfonyl, 4-chlorobutylsulfonyl, and 2-iodo-n-propylsulfonyl.

"C1-C3 alkoxycarbonyl group" refers to an alkoxycarbonyl group that has a linear, branched, or cyclic alkoxy group that contains from 1 to 3 carbon atoms, such as methoxycarbonyl, ethoxycarbonyl, isopropoxycarbonyl, and cyclopropoxycarbonyl.

"C1-C3 haloalkoxycarbonyl group" refers to an alkoxycarbonyl group that has a linear, branched, or cyclic alkoxy group that contains from 1 to 3 carbon atoms and that is substituted by one or more halogen atoms, which may be the same or different, such as trifluoromethoxycarbonyl, pentafluoroethoxycarbonyl, 2-chloroethoxycarbonyl, 2,2,2-trifluoroethoxycarbonyl, heptafluoro-n-propoxycarbonyl, heptafluoroisopropoxycarbonyl, 1,1,1,3,3,3-hexafluoro-2-propoxycarbonyl, 3-fluoro-n-propoxycarbonyl, 1-chlorocyclopropoxycarbonyl, 2-bromocyclopropoxycarbonyl, and 2-iodo-n-propyloxycarbonyl.

The 3-aminoxalylaminobenzamide derivatives represented by Formula (1) according to the invention may include one or more asymmetric carbon atoms or asymmetric centers in their structural formula, and may have two or more optical isomers. All of the optical isomers and all of the mixtures that include any of the isomers in any ratio are encompassed in the invention. The 3-aminoxalylaminobenzamide derivatives represented by Formula (1) according to the invention may have two or more geometric isomers that involve the carbon-carbon double bond in their structural formula. All of the geometric isomers and all of the mixtures that include any of the isomers in any ratio are encompassed in the invention.

In Formula (1), $R_1$ is preferably a methoxy group, a trifluoromethoxy group, a difluoromethoxy group, a trifluoromethylthio group, a trifluoromethylsulfinyl group, a trifluoromethylsulfonyl group, a chlorine atom, a bromine atom, an iodine atom, a methyl group, an ethyl group, an isopropyl group, or a trifluoromethyl group.

Preferably, $R_2$ is a chlorine atom, a bromine atom, an iodine atom, a methyl group, or an ethyl group.

Preferably, each of $R_3$ and $R_4$ is independently a C1-C4 alkyl group, a C1-C4 haloalkyl group, a C3-C4 alkenyl group, a C3-C4 haloalkenyl group, a propargyl group, or a C3-C5 cycloalkyl group, or $R_3$ and $R_4$ together form a C4-C5 alkylene group that is optionally substituted by a methyl group.

Preferably, $R_5$ is a C3-C4 haloalkyl group. Preferably, $R_6$ and $R_7$ is a hydrogen atom or a C1-C5 alkyl group.

Preferably, Y is a hydrogen atom or a halogen atom, and Z is a hydrogen atom.

In Formula (1), $R_1$ is more preferably a trifluoromethyl group, a difluoromethoxy group, a trifluoromethylthio group, a trifluoromethylsulfinyl group, or a trifluoromethylsulfonyl group, and $R_2$ is more preferably a chlorine atom, a bromine atom, an iodine atom, a methyl group, or an ethyl group.

More preferably, each of $R_3$ and $R_4$ is independently a C1-C4 alkyl group or a C1-C4 haloalkyl group, and $R_5$ is a C3-C4 haloalkyl group.

More preferably, each of $R_6$ and $R_7$ is independently a hydrogen atom or a C1-C5 alkyl group, Y is a fluorine atom, and Z is a hydrogen atom.

Preferably, the 3-aminoxalylaminobenzamide derivatives represented by Formula (1) are represented by any one of the following Formulae (2) to (26):

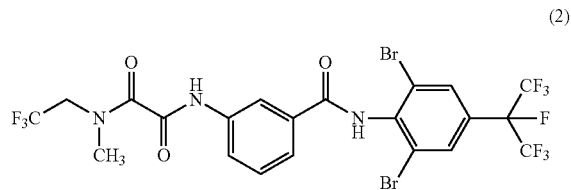

(2)

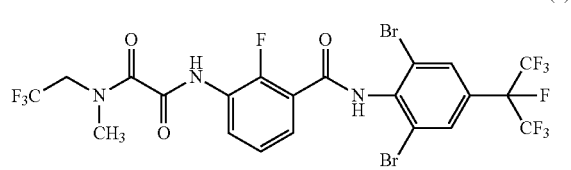

(3)

(4)
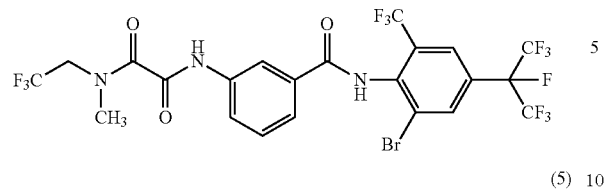
(5)
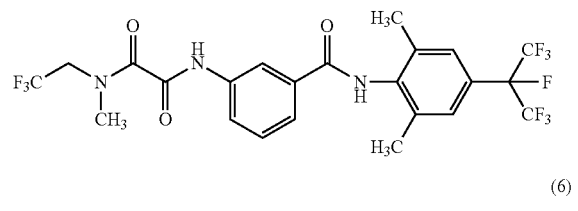
(6)
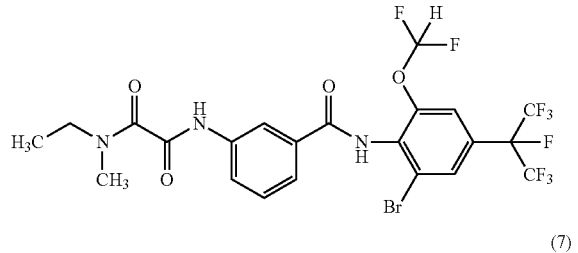
(7)
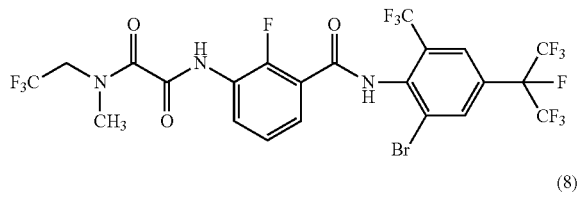
(8)
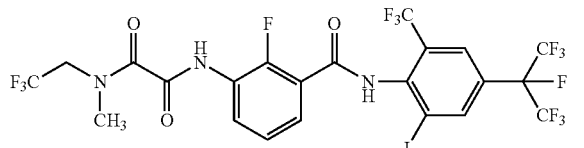
(9)
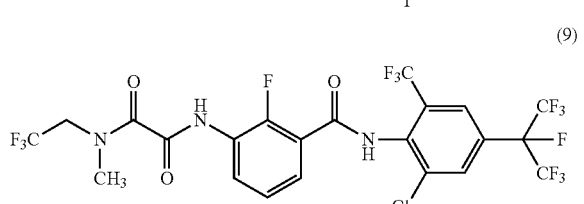
(10)
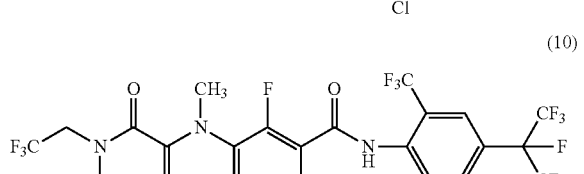
(11)
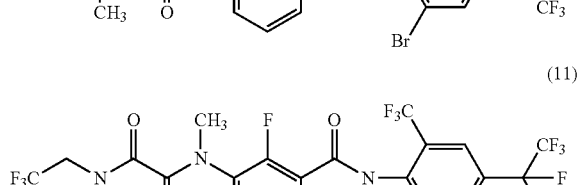
(12)
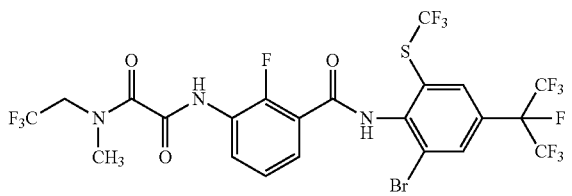
(13)
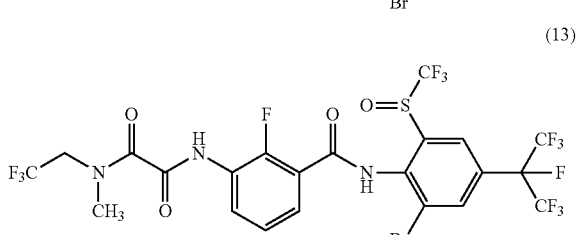
(14)
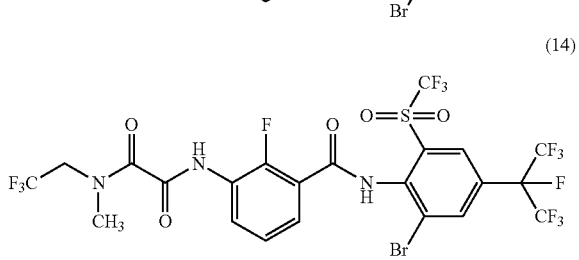
(15)
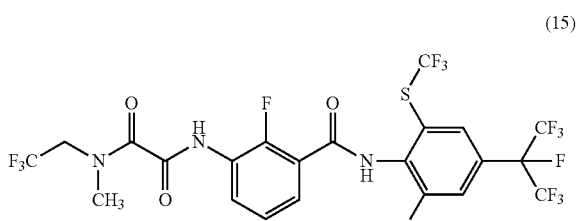
(16)
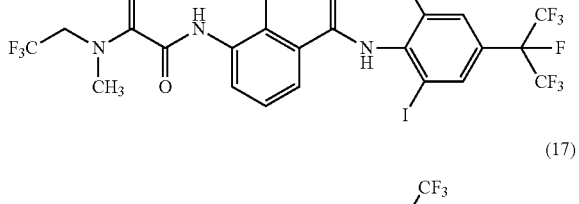
(17)
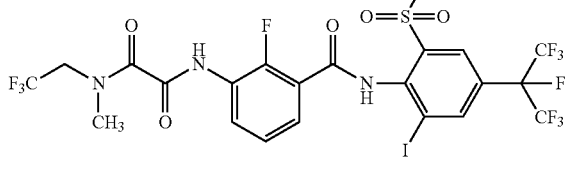
(18)
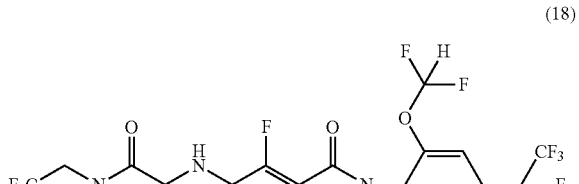

-continued

(19)
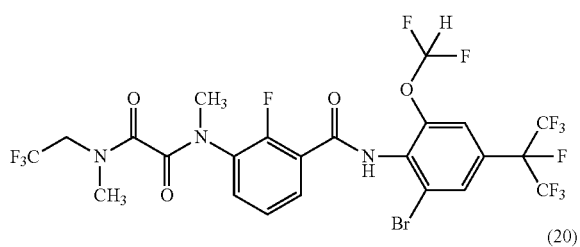

(20)
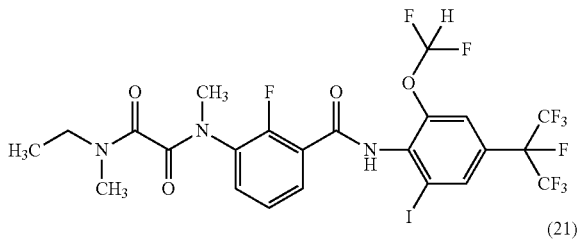

(21)
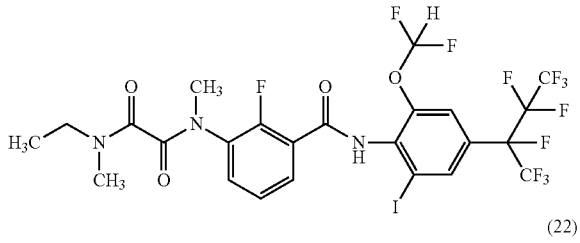

(22)
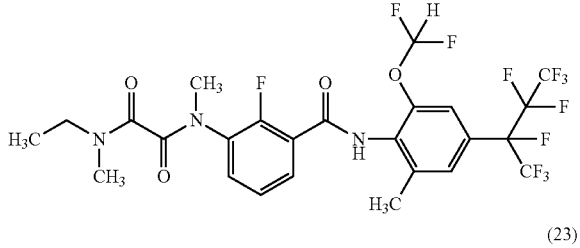

(23)
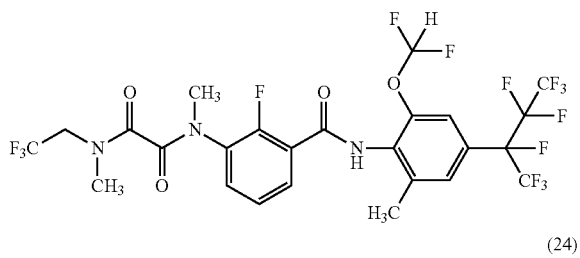

(24)
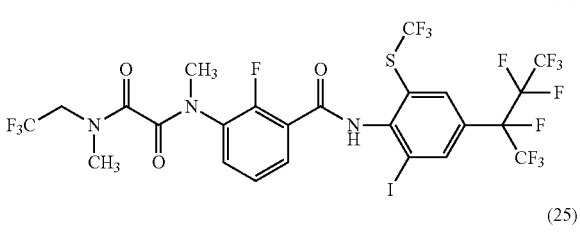

(25)
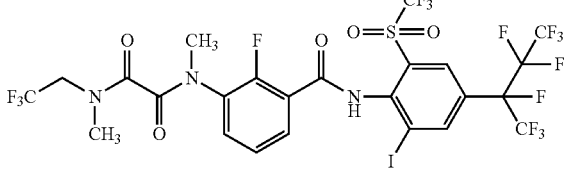

-continued

(26)
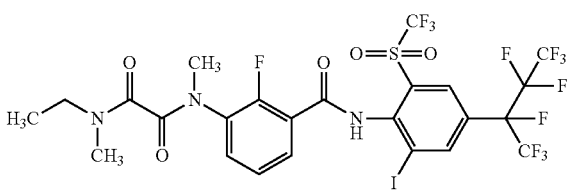

The 3-aminoxalylaminobenzamide derivatives represented by Formula (1) according to the invention can be produced in accordance with methods described in, for example, WO 2010/089881, WO 2010/090282, WO 2012/020483, WO 2012/020484, WO 2012/077221, WO 2012/164698, and WO 2010/018714.

Now, exemplary compounds of the 3-aminoxalylaminobenzamide derivatives represented by Formula (1), the derivatives being an active ingredient of the composition for exterminating an animal parasite of the invention, will be illustrated, although the invention is not limited to the compounds.

In the following tables, "n-" represents normal, "i-" represents iso, "s-" represents secondary, "t-" represents tertiary, "c-" represents cyclo, "Me" represents a methyl group, "Et" represents an ethyl group, "n-Pr" represents a normal propyl group, "i-Pr" represents an isopropyl group, "c-Pr" represents a cyclopropyl group, "n-Bu" represents a normal butyl group, "i-Bu" represents an isobutyl group, "s-Bu" represents a secondary butyl group, "t-Bu" represents a tertiary butyl group, "c-Bu" represents a cyclobutyl group, "c-Pen" represents a cyclopentyl group, "c-Hex" represents a cyclohexyl group, "allyl" represents an allyl group, and "propargyl" represents a propargyl group.

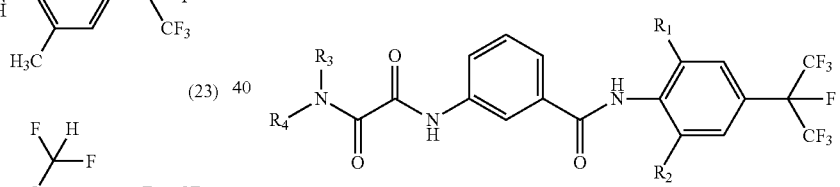

TABLE 1 (1)

| Compound No. | $R_1$ | $R_2$ | $R_3$ | $R_4$ |
|---|---|---|---|---|
| 1-1 | Me | Me | H | H |
| 1-2 | Me | Me | H | Me |
| 1-3 | Me | Me | H | Et |
| 1-4 | Me | Me | H | n-Pr |
| 1-5 | Me | Me | H | i-Pr |
| 1-6 | Me | Me | H | c-Pr |
| 1-7 | Me | Me | H | allyl |
| 1-8 | Me | Me | H | n-Bu |
| 1-9 | Me | Me | H | i-Bu |
| 1-10 | Me | Me | H | s-Bu |
| 1-11 | Me | Me | H | t-Bu |
| 1-12 | Me | Me | H | c-Bu |
| 1-13 | Me | Me | H | $CH_2$—c-Pr |
| 1-14 | Me | Me | H | $CH_2$—c-Bu |
| 1-15 | Me | Me | H | CH(Me)—n-Pr |
| 1-16 | Me | Me | H | $CH(Et)_2$ |
| 1-17 | Me | Me | H | $C(Me)_2Et$ |
| 1-18 | Me | Me | H | $CH_2CMe_3$ |
| 1-19 | Me | Me | H | c-Pen |
| 1-20 | Me | Me | H | c-Hex |

TABLE 1 (2)

| Compound No. | R$_1$ | R$_2$ | R$_3$ | R$_4$ |
|---|---|---|---|---|
| 1-21 | Me | Me | Me | He |
| 1-22 | Me | Me | Me | Et |
| 1-23 | Me | Me | Me | n-Pr |
| 1-24 | Me | Me | Me | i-Pr |
| 1-25 | Me | Me | Me | c-Pr |
| 1-26 | Me | Me | Me | allyl |
| 1-27 | Me | Me | Me | n-Bu |
| 1-28 | Me | Me | Me | t-Bu |
| 1-29 | Me | Me | Me | c-Hex |
| 1-30 | Me | Me | Et | Et |
| 1-31 | Me | Me | i-Pr | i-Pr |
| 1-32 | Me | Me | CH$_2$CH$_2$CH$_2$ | |
| 1-33 | Me | Me | CH$_2$CH$_2$CH$_2$CH$_2$ | |
| 1-34 | Me | Me | CH$_2$CH$_2$CH$_2$CH$_2$CH$_2$ | |
| 1-35 | Me | Et | H | Et |
| 1-36 | Me | Et | H | t-Bu |
| 1-37 | Me | Et | Me | Me |
| 1-38 | Me | Et | Me | Et |
| 1-39 | Me | Et | Me | n-Pr |
| 1-40 | Me | Et | Me | i-Pr |

TABLE 1 (3)

| Compound No. | R$_1$ | R$_2$ | R$_3$ | R$_4$ |
|---|---|---|---|---|
| 1-41 | Me | Et | Me | c-Pr |
| 1-42 | Me | Et | Me | allyl |
| 1-43 | Me | Et | Me | n-Bu |
| 1-44 | Me | Et | Me | t-Bu |
| 1-45 | Me | Et | Me | c-Bu |
| 1-46 | Me | Et | Me | CH$_2$CMe$_3$ |
| 1-47 | Me | Et | Me | c-Pen |
| 1-48 | Me | Et | Me | c-Hex |
| 1-49 | Me | Et | Et | Et |
| 1-50 | Me | Et | Et | t-Bu |
| 1-51 | Me | Et | CH$_2$CH$_2$CH$_2$CH$_2$ | |
| 1-52 | H | H | Me | Me |
| 1-53 | H | Me | Me | Me |
| 1-54 | H | Et | Me | Me |
| 1-55 | H | Et | Me | Et |
| 1-56 | Et | Et | Me | Me |
| 1-57 | Et | Et | Me | Et |
| 1-58 | Et | Et | Me | t-Bu |
| 1-59 | Me | Cl | Me | Me |
| 1-60 | Me | Cl | Me | Et |
| 1-61 | Me | Cl | Me | t-Bu |
| 1-62 | Me | Br | Me | Et |
| 1-63 | Me | Br | Me | t-Bu |
| 1-64 | Me | I | Me | Et |
| 1-65 | Me | I | Me | t-Bu |
| 1-66 | Et | Cl | Me | Me |
| 1-67 | Et | Cl | Me | Et |
| 1-68 | Et | Cl | Me | t-Bu |
| 1-69 | Et | Br | Me | Et |
| 1-70 | Et | Br | Me | t-Bu |
| 1-71 | Et | I | Me | Et |
| 1-72 | Et | I | Me | t-Bu |
| 1-73 | i-Pr | Cl | Me | Et |
| 1-74 | i-Pr | Br | Me | Et |
| 1-75 | Me | Me | H | (CH$_2$)$_2$Cl |
| 1-76 | Me | Et | H | (CH$_2$)$_2$Cl |
| 1-77 | Et | Et | H | (CH$_2$)$_2$Cl |
| 1-78 | Me | Et | Me | (CH$_2$)$_2$Cl |
| 1-79 | Et | Br | Me | (CH$_2$)$_2$Cl |
| 1-80 | Me | Mr | H | (CH$_2$)$_2$Br |

TABLE 1 (4)

| Compound No. | R$_1$ | R$_2$ | R$_3$ | R$_4$ |
|---|---|---|---|---|
| 1-81 | Me | Et | Me | (CH$_2$)$_2$Br |
| 1-82 | Et | Br | Me | (CH$_2$)$_2$Br |
| 1-83 | Me | Me | H | (CH$_2$)$_3$Cl |
| 1-84 | Me | Me | H | (CH$_2$)$_3$Br |
| 1-85 | Me | Et | H | CH$_2$CF$_3$ |
| 1-86 | Me | Me | Me | CH$_2$CF$_3$ |
| 1-87 | Me | Et | Me | CH$_2$CF$_3$ |
| 1-88 | Et | Et | Me | CH$_2$CF$_3$ |
| 1-89 | Me | Cl | Me | CH$_2$CF$_3$ |
| 1-90 | Me | Br | Me | CH$_2$CF$_3$ |
| 1-91 | Me | I | Me | CH$_2$CF$_3$ |
| 1-92 | Et | Cl | Me | CH$_2$CF$_3$ |
| 1-93 | Et | Br | Me | CH$_2$CF$_3$ |
| 1-94 | Et | I | Me | CH$_2$CF$_3$ |
| 1-95 | i-Pr | Cl | Me | CH$_2$CF$_3$ |
| 1-96 | i-Pr | Br | Me | CH$_2$CF$_3$ |
| 1-97 | Me | Et | Et | CH$_2$CF$_3$ |
| 1-98 | Me | Et | allyl | CH$_2$CF$_3$ |
| 1-99 | Me | Et | CH$_2$CHF$_2$ | CH$_2$CF$_3$ |
| 1-100 | Me | Et | Me | CH$_2$CHF$_2$ |
| 1-101 | Me | Et | Et | CH$_2$CHF$_2$ |
| 1-102 | Me | Et | CH$_2$CH$_2$F | CH$_2$CHF$_2$ |
| 1-103 | Me | Et | Me | CH$_2$CH$_2$F |
| 1-104 | Me | Et | Et | CH$_2$CH$_2$F |
| 1-105 | Me | Et | Me | CH$_2$CF$_2$CF$_3$ |
| 1-106 | Me | Et | Me | CHMeCF$_3$ |
| 1-107 | Me | I | Me | CHMeCF$_3$ |
| 1-108 | Et | Br | Me | CHMeCF$_3$ |
| 1-109 | Et | Br | Me | CH$_2$CHF$_2$ |
| 1-110 | Et | Br | Me | CH$_2$CH$_2$F |
| 1-111 | OMe | Cl | Me | Et |
| 1-112 | OMe | Cl | Me | CH$_2$CF$_3$ |
| 1-113 | OMe | Br | Me | Et |
| 1-114 | OMe | Br | Me | CH$_2$CF$_3$ |
| 1-115 | OCF$_3$ | Cl | Me | Et |
| 1-116 | OCF$_3$ | Cl | Me | CH$_2$CF$_3$ |

TABLE 1 (5)

| Compound No. | R$_1$ | R$_2$ | R$_3$ | R$_4$ |
|---|---|---|---|---|
| 1-117 | CF$_3$ | Cl | Me | t-Bu |
| 1-118 | CF$_3$ | Cl | Me | CH$_2$CF$_3$ |
| 1-119 | CF$_3$ | Br | Me | Et |
| 1-120 | CF$_3$ | Br | Me | n-Pr |
| 1-121 | CF$_3$ | Br | Me | i-Pr |
| 1-122 | CF$_3$ | Br | Me | c-Pr |
| 1-123 | CF$_3$ | Br | Me | allyl |
| 1-124 | CF$_3$ | Br | Me | propargyl |
| 1-125 | CF$_3$ | Br | Me | n-Bu |
| 1-126 | CF$_3$ | Br | CH$_2$CH$_2$CH$_2$CH$_2$ | |
| 1-127 | CF$_3$ | Br | Me | t-Bu |
| 1-128 | CF$_3$ | Br | Me | c-Pen |
| 1-129 | CF$_3$ | Br | CHMeCH$_2$CH$_2$CH$_2$ | |
| 1-130 | CF$_3$ | Br | Me | CH2CH$_2$F |
| 1-131 | CF$_3$ | Br | Me | CH$_2$CHF$_2$ |
| 1-132 | CF$_3$ | Br | Me | CH$_2$CF$_3$ |
| 1-133 | CF$_3$ | Br | Me | CHMeCF$_3$ |
| 1-134 | CF$_3$ | Br | Me | CH$_2$CCl=CH$_2$ |
| 1-135 | CF$_3$ | I | Me | t-Bu |
| 1-136 | CF$_3$ | I | Me | CH$_2$CF$_3$ |
| 1-137 | CF$_3$ | I | Me | CHMeCF$_3$ |
| 1-138 | SCF$_3$ | Br | Me | t-Bu |
| 1-139 | SOCF$_3$ | Br | Me | t-Bu |
| 1-140 | SO$_2$CF$_3$ | Br | Me | t-Bu |
| 1-141 | SCF$_3$ | Br | Me | CH$_2$CF$_3$ |
| 1-142 | SOCF$_3$ | Br | Me | CH$_2$CF$_3$ |
| 1-143 | SO$_2$CF$_3$ | Br | Me | CH$_2$CF$_3$ |

TABLE 1 (6)

| Compound No. | R$_1$ | R$_2$ | R$_3$ | R$_4$ |
|---|---|---|---|---|
| 1-144 | Br | Br | Me | Et |
| 1-145 | Br | Br | Me | n-Pr |
| 1-146 | Br | Br | Me | c-Pr |

TABLE 1 (6)-continued

| Compound No. | R₁ | R₂ | R₃ | R₄ |
|---|---|---|---|---|
| 1-147 | Br | Br | Me | allyl |
| 1-148 | Br | Br | Me | propargyl |
| 1-149 | Br | Br | Me | n-Bu |
| 1-150 | Br | Br | CH₂CH₂CH₂CH₂ | |
| 1-151 | Br | Br | Me | t-Bu |
| 1-152 | Br | Br | Me | CH₂CH₂F |
| 1-153 | Br | Br | Me | CH₂CHF₂ |
| 1-154 | Br | Br | Me | CH₂CF₃ |
| 1-155 | Br | Br | Me | CHMeCF₃ |
| 1-156 | Br | Br | Et | Et |
| 1-157 | Br | I | Me | CH₂CF₃ |
| 1-158 | I | I | Me | CH₂CF₃ |

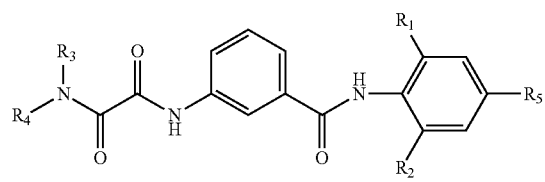

TABLE 2 (1)

| Compound No. | R₁ | R₂ | R₃ | R₄ | R₅ |
|---|---|---|---|---|---|
| 2-1 | Me | Et | Me | CH₂CF₃ | CH₂CF₃ |
| 2-2 | Me | Et | Me | t-Bu | CF₂CF₂CF₃ |
| 2-3 | Me | Et | Me | CH₂CF₃ | CF₂CF₂CF₃ |
| 2-4 | Me | Et | Me | t-Bu | CF(CF₃)CF₂CF₃ |
| 2-5 | Me | Et | Me | CH₂CF₃ | CF(CF₃)CF₂CF₃ |
| 2-6 | Et | Cl | Me | t-Bu | CF(CF₃)CF₂CF₃ |
| 2-7 | Et | Cl | Me | CH₂CF₃ | CF(CF₃)CF₂CF₃ |
| 2-8 | Et | Br | Me | t-Bu | CF(CF₃)CF₂CF₃ |
| 2-9 | Et | Br | Me | CH₂CF₃ | CF(CF₃)CF₂CF₃ |
| 2-10 | Me | Et | Me | t-Bu | CF₂CF₂Br |
| 2-11 | Me | Et | Me | CH₂CF₃ | CF₂CF₂Br |
| 2-12 | Et | Br | Me | CH₂CF₃ | CF₂CF₂Br |
| 2-13 | Me | Me | Me | Et | CF(CF₃)CF₂Br |
| 2-14 | Me | Me | Me | t-Bu | CF(CF₃)CF₂Br |
| 2-15 | Me | Me | Me | CH₂CF₃ | CF(CF₃)CF₂Br |
| 2-16 | Me | Et | Me | Et | CF(CF₃)CF₂Br |
| 2-17 | Me | Et | Me | t-Bu | CF(CF₃)CF₂Br |
| 2-18 | Me | Et | Me | CH₂CF₃ | CF(CF₃)CF₂Br |
| 2-19 | Me | Cl | Me | t-Bu | CF(CF₃)CF₂Br |
| 2-20 | Me | Cl | Me | CH₂CF₃ | CF(CF₃)CF₂Br |
| 2-21 | Me | Br | Me | t-Bu | CF(CF₃)CF₂Br |
| 2-22 | Me | Br | Me | CH₂CF₃ | CF(CF₃)CF₂Br |
| 2-23 | Me | I | Me | t-Bu | CF(CF₃)CF₂Br |
| 2-24 | Me | I | Me | CH₂CF₃ | CF(CF₃)CF₂Br |
| 2-25 | Et | Cl | Me | t-Bu | CF(CF₃)CF₂Br |
| 2-26 | Et | Cl | Me | CH₂CF₃ | CF(CF₃)CF₂Br |
| 2-27 | Et | Br | Me | t-Bu | CF(CF₃)CF₂Br |
| 2-28 | Et | Br | Me | CH₂CF₃ | CF(CF₃)CF₂Br |
| 2-29 | Et | I | Me | t-Bu | CF(CF₃)CF₂Br |
| 2-30 | Et | I | Me | CH₂CF₃ | CF(CF₃)CF₂Br |

TABLE 2 (2)

| Compound No. | R₁ | R₂ | R₃ | R₄ | R₅ |
|---|---|---|---|---|---|
| 2-31 | CF₃ | Br | Me | t-Bu | CF₂CF₂CF₃ |
| 2-32 | CF₃ | Br | Me | CH₂CF₃ | CF₂CF₂CF₃ |
| 2-33 | CF₃ | Br | Me | t-Bu | CF(CF₃)CF₂CF₃ |
| 2-34 | CF₃ | Br | Me | CH₂CF₃ | CF(CF₃)CF₂CF₃ |
| 2-35 | CF₃ | Br | Me | t-Bu | CF(CF₃)CF₂Br |
| 2-36 | CF₃ | Br | Me | CH₂CF₃ | CF(CF₃)CF₂Br |

TABLE 2 (3)

| Compound No. | R₁ | R₂ | R₃ | R₄ | R₅ |
|---|---|---|---|---|---|
| 2-37 | Cl | Cl | Me | CH₂CF₃ | CF(CF₃)CF₂Br |
| 2-38 | Br | Br | Me | t-Bu | CF(CF₃)CF₂CF₃ |
| 2-39 | Br | Br | Me | CH₂CF₃ | CF(CF₃)CF₂CF₃ |
| 2-40 | Br | Br | Me | t-Bu | CF(CF₃)CF₂Br |
| 2-41 | Br | Br | Me | CH₂CF₃ | CF(CF₃)CF₂Br |
| 2-42 | Br | Br | Me | CHMeCF₃ | CF(CF₃)CF₂Br |
| 2-43 | I | I | Me | CH₂CF₃ | CF(CF₃)CF₂Br |

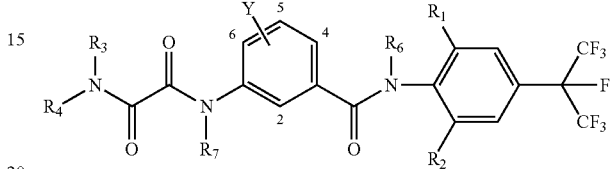

TABLE 3 (1)

| Compound No. | R₁ | R₂ | R₃ | R₄ | R₆ | R₇ | Y |
|---|---|---|---|---|---|---|---|
| 3-1 | Me | Et | Me | t-Bu | Me | H | H |
| 3-2 | Me | Et | Me | CH₂CF₃ | Me | H | H |
| 3-3 | Me | Et | Me | CH₂CF₃ | H | Me | H |
| 3-4 | Me | Et | Me | Et | H | H | 6-F |
| 3-5 | Me | Et | Me | CH₂CF₃ | H | H | 6-F |

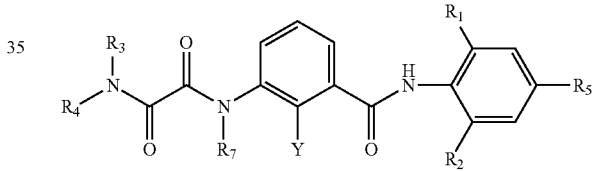

TABLE 4 (1)

| Compound No. | R₁ | R₂ | R₃ | R₄ | R₅ | R₇ | Y |
|---|---|---|---|---|---|---|---|
| 4-1 | Me | Me | Me | CH₂CF₃ | CF(CF₃)₂ | H | F |
| 4-2 | Me | Et | Me | Me | CF(CF₃)₂ | H | F |
| 4-3 | Me | Et | Me | Et | CF(CF₃)₂ | H | F |
| 4-4 | Me | Et | Me | n-Pr | CF(CF₃)₂ | H | F |
| 4-5 | Me | Et | Me | i-Pr | CF(CF₃)₂ | H | F |
| 4-6 | Me | Et | Me | c-Pr | CF(CF₃)₂ | H | F |
| 4-7 | Me | Et | Me | allyl | CF(CF₃)₂ | H | F |
| 4-8 | Me | Et | Me | propargyl | CF(CF₃)₂ | H | F |
| 4-9 | Me | Et | Me | n-Bu | CF(CF₃)₂ | H | F |
| 4-10 | Me | Et | Me | t-Bu | CF(CF₃)₂ | H | F |
| 4-11 | Me | Et | Me | c-Pen | CF(CF₃)₂ | H | F |
| 4-12 | Me | Et | Et | Et | CF(CF₃)₂ | H | F |
| 4-13 | Me | Et | | CH₂CH₂ | CF(CF₃)₂ | H | F |
| 4-14 | Me | Et | | CH₂CH₂CH₂CH₂ | CF(CF₃)₂ | H | F |
| 4-15 | Me | Et | | CH₂CH₂CH₂CH₂CH₂ | CF(CF₃)₂ | H | F |
| 4-16 | Me | Et | Me | CH₂CH₂F | CF(CF₃)₂ | H | F |
| 4-17 | Me | Et | Me | CH₂CHF₂ | CF(CF₃)₂ | H | F |
| 4-18 | Me | Et | Me | CH₂CF₃ | CF(CF₃)₂ | H | F |
| 4-19 | Me | Et | Me | CHMeCF₃ | CF(CF₃)₂ | H | F |
| 4-20 | Et | Et | Me | CH₂CF₃ | CF(CF₃)₂ | H | F |
| 4-21 | Me | Cl | Me | CH₂CF₃ | CF(CF₃)₂ | H | F |
| 4-22 | Me | Br | Me | CH₂CF₃ | CF(CF₃)₂ | H | F |
| 4-23 | Me | I | Me | CH₂CF₃ | CF(CF₃)₂ | H | F |
| 4-24 | Et | Cl | Me | CH₂CF₃ | CF(CF₃)₂ | H | F |
| 4-25 | Et | Br | Me | Et | CF(CF₃)₂ | H | F |
| 4-26 | Et | Br | Me | t-Bu | CF(CF₃)₂ | H | F |

TABLE 4 (1)-continued

| Compound No. | R₁ | R₂ | R₃ | R₄ | R₅ | R₇ | Y |
|---|---|---|---|---|---|---|---|
| 4-27 | Et | Br | Me | CH₂CH₂F | CF(CF₃)₂ | H | F |
| 4-28 | Et | Br | Me | CH₂CHF₂ | CF(CF₃)₂ | H | F |
| 4-29 | Et | Br | Me | CH₂CF₃ | CF(CF₃)₂ | H | F |
| 4-30 | Et | Br | Me | CHMeCF₃ | CF(CF₃)₂ | H | F |

TABLE 4 (2)

| Compound No. | R₁ | R₂ | R₃ | R₄ | R₅ | R₇ | Y |
|---|---|---|---|---|---|---|---|
| 4-31 | Et | I | Me | CH₂CF₃ | CF(CF₃)₂ | H | F |
| 4-32 | OMe | Cl | Me | CH₂CF₃ | CF(CF₃)₂ | H | F |
| 4-33 | OMe | Br | Me | CH₂CF₃ | CF(CF₃)₂ | H | F |
| 4-34 | OMe | I | Me | CH₂CF₃ | CF(CF₃)₂ | H | F |
| 4-35 | OCF₃ | Cl | Me | CH₂CF₃ | CF(CF₃)₂ | H | F |
| 4-36 | OCF₃ | Br | Me | CH₂CF₃ | CF(CF₃)₂ | H | F |
| 4-37 | OCF₃ | I | Me | CH₂CF₃ | CF(CF₃)₂ | H | F |
| 4-38 | Me | Et | Me | Et | CF(CF₃)₂ | Me | F |
| 4-39 | Me | Et | Me | t-Bu | CF(CF₃)₂ | Me | F |
| 4-40 | Me | Et | Me | CH₂CH₂F | CF(CF₃)₂ | Me | F |
| 4-41 | Me | Et | Me | CH₂CHF₂ | CF(CF₃)₂ | Me | F |
| 4-42 | Me | Et | Me | CH₂CF₃ | CF(CF₃)₂ | Me | F |
| 4-43 | Me | Et | Me | CHMeCF₃ | CF(CF₃)₂ | Me | F |
| 4-44 | Et | Br | Me | Et | CF(CF₃)₂ | Me | F |
| 4-45 | Et | Br | Me | CH₂CF₃ | CF(CF₃)₂ | Me | F |
| 4-46 | Me | Me | Me | CH₂CF₃ | CF(CF₃)CF₂Br | H | F |
| 4-47 | Me | Et | Me | CH₂CF₃ | CF(CF₃)CF₂Br | H | F |
| 4-48 | Et | Et | Me | CH₂CF₃ | CF(CF₃)CF₂Br | H | F |
| 4-49 | Me | Cl | Me | CH₂CF₃ | CF(CF₃)CF₂Br | H | F |
| 4-50 | Me | Br | Me | CH₂CF₃ | CF(CF₃)CF₂Br | H | F |
| 4-51 | Me | I | Me | CH₂CF₃ | CF(CF₃)CF₂Br | H | F |
| 4-52 | Et | Cl | Me | CH₂CF₃ | CF(CF₃)CF₂Br | H | F |
| 4-53 | Et | Br | Me | Et | CF(CF₃)CF₂Br | H | F |
| 4-54 | Et | Br | Me | CH₂CF₃ | CF(CF₃)CF₂Br | H | F |
| 4-55 | Et | I | Me | CH₂CF₃ | CF(CF₃)CF₂Br | H | F |
| 4-56 | Me | Me | Me | CH₂CF₃ | CF(CF₃)CF₂CF₃ | H | F |
| 4-57 | Me | Et | Me | CH₂CF₃ | CF(CF₃)CF₂CF₃ | H | F |
| 4-58 | Et | Et | Me | CH₂CF₃ | CF(CF₃)CF₂CF₃ | H | F |
| 4-59 | Me | Cl | Me | CH₂CF₃ | CF(CF₃)CF₂CF₃ | H | F |
| 4-60 | Me | Br | Me | CH₂CF₃ | CF(CF₃)CF₂CF₃ | H | F |
| 4-61 | Me | I | Me | CH₂CF₃ | CF(CF₃)CF₂CF₃ | H | F |
| 4-62 | Et | Cl | Me | CH₂CF₃ | CF(CF₃)CF₂CF₃ | H | F |
| 4-63 | Et | Br | Me | CH₂CF₃ | CF(CF₃)CF₂CF₃ | H | F |
| 4-64 | Et | I | Me | CH₂CF₃ | CF(CF₃)CF₂CF₃ | H | F |
| 4-65 | Me | Et | Me | CH₂CF₃ | CF(CF₃)₂ | H | Cl |
| 4-66 | Br | Br | Me | CH₂CF₃ | CF(CF₃)₂ | H | F |

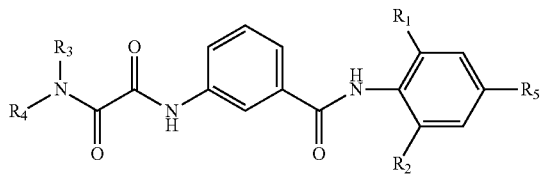

TABLE 5 (1)

| Compound No. | R₁ | R₂ | R₃ | R₄ | R₅ |
|---|---|---|---|---|---|
| 5-1 | OCHF₂ | Cl | Me | Me | CF(CF₃)₂ |
| 5-2 | OCHF₂ | Cl | Me | Et | CF(CF₃)₂ |
| 5-3 | OCHF₂ | Cl | Me | n-Pr | CF(CF₃)₂ |
| 5-4 | OCHF₂ | Cl | Me | i-Pr | CF(CF₃)₂ |
| 5-5 | OCHF₂ | Cl | Me | c-Pr | CF(CF₃)₂ |
| 5-6 | OCHF₂ | Cl | Me | allyl | CF(CF₃)₂ |
| 5-7 | OCHF₂ | Cl | Me | propargyl | CF(CF₃)₂ |
| 5-8 | OCHF₂ | Cl | Me | n-Bu | CF(CF₃)₂ |
| 5-9 | OCHF₂ | Cl | Me | t-Bu | CF(CF₃)₂ |
| 5-10 | OCHF₂ | Cl | Me | CH₂CH₂F | CF(CF₃)₂ |
| 5-11 | OCHF₂ | Cl | Me | CH₂CHF₂ | CF(CF₃)₂ |
| 5-12 | OCHF₂ | Cl | Me | CH₂CF₃ | CF(CF₃)₂ |
| 5-13 | OCHF₂ | Cl | Me | CHMeCF₃ | CF(CF₃)₂ |
| 5-14 | OCHF₂ | Br | Me | Me | CF(CF₃)₂ |
| 5-15 | OCHF₂ | Br | Me | Et | CF(CF₃)₂ |
| 5-16 | OCHF₂ | Br | Me | n-Pr | CF(CF₃)₂ |
| 5-17 | OCHF₂ | Br | Me | i-Pr | CF(CF₃)₂ |
| 5-18 | OCHF₂ | Br | Me | c-Pr | CF(CF₃)₂ |
| 5-19 | OCHF₂ | Br | Me | allyl | CF(CF₃)₂ |
| 5-20 | OCHF₂ | Br | Me | propargyl | CF(CF₃)₂ |
| 5-21 | OCHF₂ | Br | Me | n-Bu | CF(CF₃)₂ |
| 5-22 | OCHF₂ | Br | CH₂CH₂CH₂CH₂ | | CF(CF₃)₂ |
| 5-23 | OCHF₂ | Br | Me | cBu | CF(CF₃)₂ |
| 5-24 | OCHF₂ | Br | Me | c-Pen | CF(CF₃)₂ |
| 5-25 | OCHF₂ | Br | CH₂CH₂CH₂CH₂CHMe | | CF(CF₃)₂ |
| 5-26 | OCHF₂ | Br | Me | CH₂CH₂F | CF(CF₃)₂ |
| 5-27 | OCHF₂ | Br | Me | CH₂CHF₂ | CF(CF₃)₂ |
| 5-28 | OCHF₂ | Br | Me | CH₂CF₃ | CF(CF₃)₂ |
| 5-29 | OCHF₂ | Br | Me | CHMeCF₃ | CF(CF₃)₂ |
| 5-30 | OCHF₂ | Br | CH₂CH₂CH₂CHCF₃ | | CF(CF₃)₂ |
| 5-31 | OCHF₂ | Br | Me | CH₂CCl=CH₂ | CF(CF₃)₂ |

TABLE 5 (2)

| Compound No. | R₁ | R₂ | R₃ | R₄ | R₅ |
|---|---|---|---|---|---|
| 5-32 | OCHF₂ | I | Me | Me | CF(CF₃)₂ |
| 5-33 | OCHF₂ | I | Me | Et | CF(CF₃)₂ |
| 5-34 | OCHF₂ | I | Me | n-Pr | CF(CF₃)₂ |
| 5-35 | OCHF₂ | I | Me | i-Pr | CF(CF₃)₂ |
| 5-36 | OCHF₂ | I | Me | c-Pr | CF(CF₃)₂ |
| 5-37 | OCHF₂ | I | Me | allyl | CF(CF₃)₂ |
| 5-38 | OCHF₂ | I | Me | propargyl | CF(CF₃)₂ |
| 5-39 | OCHF₂ | I | Me | n-Bu | CF(CF₃)₂ |
| 5-40 | OCHF₂ | I | CH₂CH₂CH₂CH₂ | | CF(CF₃)₂ |
| 5-41 | OCHF₂ | I | Me | t-Bu | CF(CF₃)₂ |
| 5-42 | OCHF₂ | I | Me | c-Pen | CF(CF₃)₂ |
| 5-43 | OCHF₂ | I | CH₂CH₂CH₂CH₂CHMe | | CF(CF₃)₂ |
| 5-44 | OCHF₂ | I | Me | CH₂CH₂F | CF(CF₃)₂ |
| 5-45 | OCHF₂ | I | Me | CH₂CHF₂ | CF(CF₃)₂ |
| 5-46 | OCHF₂ | I | Me | CH₂CF₃ | CF(CF₃)₂ |
| 5-47 | OCHF₂ | I | Me | CHMeCF₃ | CF(CF₃)₂ |
| 5-48 | OCHF₂ | I | Me | CH₂CCl=CH₂ | CF(CF₃)₂ |
| 5-49 | OCHF₂ | Me | Me | Me | CF(CF₃)₂ |
| 5-50 | OCHF₂ | Me | Me | Et | CF(CF₃)₂ |
| 5-51 | OCHF₂ | Me | Me | n-Pr | CF(CF₃)₂ |
| 5-52 | OCHF₂ | Me | Me | i-Pr | CF(CF₃)₂ |
| 5-53 | OCHF₂ | Me | Me | c-Pr | CF(CF₃)₂ |
| 5-54 | OCHF₂ | Me | Me | allyl | CF(CF₃)₂ |
| 5-55 | OCHF₂ | Me | Me | propargyl | CF(CF₃)₂ |
| 5-56 | OCHF₂ | Me | Me | n-Bu | CF(CF₃)₂ |
| 5-57 | OCHF₂ | Me | CH₂CH₂CH₂CH₂ | | CF(CF₃)₂ |
| 5-58 | OCHF₂ | Me | Me | t-Bu | CF(CF₃)₂ |
| 5-59 | OCHF₂ | Me | Me | c-Pen | CF(CF₃)₂ |
| 5-60 | OCHF₂ | Me | CH₂CH₂CH₂CH₂CHMe | | CF(CF₃)₂ |
| 5-61 | OCHF₂ | Me | Me | CH₂CH₂F | CF(CF₃)₂ |
| 5-62 | OCHF₂ | Me | Me | CH₂CHF₂ | CF(CF₃)₂ |
| 5-63 | OCHF₂ | Me | Me | CH₂CF₃ | CF(CF₃)₂ |
| 5-64 | OCHF₂ | Me | Me | CHMeCF₃ | CF(CF₃)₂ |
| 5-65 | OCHF₂ | Me | Me | CH₂CCl=CH₂ | CF(CF₃)₂ |

TABLE 5 (3)

| Compound No. | R₁ | R₂ | R₃ | R₄ | R₅ |
|---|---|---|---|---|---|
| 5-66 | OCHF₂ | Br | Me | Me | CF(CF₃)CF₂Br |
| 5-67 | OCHF₂ | Br | Me | Et | CF(CF₃)CF₂Br |
| 5-68 | OCHF₂ | Br | Me | n-Pr | CF(CF₃)CF₂Br |
| 5-69 | OCHF₂ | Br | Me | i-Pr | CF(CF₃)CF₂Br |
| 5-70 | OCHF₂ | Br | Me | c-Pr | CF(CF₃)CF₂Br |
| 5-71 | OCHF₂ | Br | Me | allyl | CF(CF₃)CF₂Br |
| 5-72 | OCHF₂ | Br | Me | propargyl | CF(CF₃)CF₂Br |
| 5-73 | OCHF₂ | Br | Me | n-Bu | CF(CF₃)CF₂Br |
| 5-74 | OCHF₂ | Br | CH₂CH₂CH₂CH₂ | | CF(CF₃)CF₂Br |

TABLE 5 (3)-continued

| Compound No. | $R_1$ | $R_2$ | $R_3$ | $R_4$ | $R_5$ |
|---|---|---|---|---|---|
| 5-75 | $OCHF_2$ | Br | Me | t-Bu | $CF(CF_3)CF_2Br$ |
| 5-76 | $OCHF_2$ | Br | Me | c-Pen | $CF(CF_3)CF_2Br$ |
| 5-77 | $OCHF_2$ | Br | Me | $CH_2CH_2F$ | $CF(CF_3)CF_2Br$ |
| 5-78 | $OCHF_2$ | Br | Me | $CH_2CHF_2$ | $CF(CF_3)CF_2Br$ |
| 5-79 | $OCHF_2$ | Br | Me | $CH_2CF_3$ | $CF(CF_3)CF_2Br$ |
| 5-80 | $OCHF_2$ | Br | Me | $CHMeCF_3$ | $CF(CF_3)CF_2Br$ |
| 5-81 | $OCHF_2$ | Br | Me | Me | $CF(CF_3)CF_2CF_3$ |
| 5-82 | $OCHF_2$ | Br | Me | Et | $CF(CF_3)CF_2CF_3$ |
| 5-83 | $OCHF_2$ | Br | Me | n-Pr | $CF(CF_3)CF_2CF_3$ |
| 5-84 | $OCHF_2$ | Br | Me | i-Pr | $CF(CF_3)CF_2CF_3$ |
| 5-85 | $OCHF_2$ | Br | Me | c-Pr | $CF(CF_3)CF_2CF_3$ |
| 5-86 | $OCHF_2$ | Br | Me | allyl | $CF(CF_3)CF_2CF_3$ |
| 5-87 | $OCHF_2$ | Br | Me | propargyl | $CF(CF_3)CF_2CF_3$ |
| 5-88 | $OCHF_2$ | Br | Me | n-Bu | $CF(CF_3)CF_2CF_3$ |
| 5-89 | $OCHF_2$ | Br | $CH_2CH_2CH_2CH_2$ | | $CF(CF_3)CF_2CF_3$ |
| 5-90 | $OCHF_2$ | Br | Me | t-Bu | $CF(CF_3)CF_2CF_3$ |
| 5-91 | $OCHF_2$ | Br | Me | c-Pen | $CF(CF_3)CF_2CF_3$ |
| 5-92 | $OCHF_2$ | Br | Me | $CH_2CH_2F$ | $CF(CF_3)CF_2CF_3$ |
| 5-93 | $OCHF_2$ | Br | Me | $CH_2CHF_2$ | $CF(CF_3)CF_2CF_3$ |
| 5-94 | $OCHF_2$ | Br | Me | $CH_2CF_3$ | $CF(CF_3)CF_2CF_3$ |
| 5-95 | $OCHF_2$ | Br | Me | $CHMeCF_3$ | $CF(CF_3)CF_2CF_3$ |

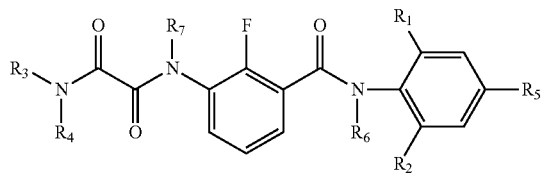

TABLE 6 (1)

| Compound No. | $R_1$ | $R_2$ | $R_3$ | $R_4$ | $R_5$ | $R_6$ | $R_7$ |
|---|---|---|---|---|---|---|---|
| 6-1 | $CF_3$ | Br | $CH_2CF_3$ | $CH_3$ | $CF(CF_3)_2$ | H | H |
| 6-2 | $CF_3$ | I | $CH_2CF_3$ | $CH_3$ | $CF(CF_3)_2$ | H | H |
| 6-3 | $CF_3$ | Cl | $CH_2CF_3$ | $CH_3$ | $CF(CF_3)_2$ | H | H |
| 6-4 | $CF_3$ | Br | $CH_2CF_3$ | $CH_3$ | $CF(CF_3)_2$ | H | $CH_3$ |
| 6-5 | $CF_3$ | I | $CH_2CF_3$ | $CH_3$ | $CF(CF_3)_2$ | H | $CH_3$ |
| 6-6 | $SCF_3$ | Br | $CH_2CF_3$ | $CH_3$ | $CF(CF_3)_2$ | H | H |
| 6-7 | $SOCF_3$ | Br | $CH_2CF_3$ | $CH_3$ | $CF(CF_3)_2$ | H | H |
| 6-8 | $SO_2CF_3$ | Br | $CH_2CF_3$ | $CH_3$ | $CF(CF_3)_2$ | H | H |
| 6-9 | $SCF_3$ | I | $CH_2CF_3$ | $CH_3$ | $CF(CF_3)_2$ | H | H |
| 6-10 | SOCF3 | I | $CH_2CF_3$ | $CH_3$ | $CF(CF_3)_2$ | H | H |
| 6-11 | $SO_2CF_3$ | I | $CH_2CF_3$ | $CH_3$ | $CF(CF_3)_2$ | H | H |
| 6-12 | $OCF_2H$ | Br | $CH_2CF_3$ | $CH_3$ | $CF(CF_3)_2$ | H | H |
| 6-13 | $OCF_2H$ | Br | $CH_2CF_3$ | $CH_3$ | $CF(CF_3)_2$ | H | $CH_3$ |
| 6-14 | $OCF_2H$ | I | $CH_2CH_3$ | $CH_3$ | $CF(CF_3)_2$ | H | $CH_3$ |
| 6-15 | $OCF_2H$ | I | $CH_2CH_3$ | $CH_3$ | $CF(CF_3)CF_2CF_3$ | H | $CH_3$ |
| 6-16 | $OCF_2H$ | $CH_3$ | $CH_2CH_3$ | $CH_3$ | $CF(CF_3)CF_2CF_3$ | H | $CH_3$ |
| 6-17 | $OCF_2H$ | $CH_3$ | $CH_2CH_3$ | $CH_3$ | $CF(CF_3)CF_2CF_3$ | H | $CH_3$ |
| 6-18 | $SCF_3$ | I | $CH_2CF_3$ | $CH_3$ | $CF(CF_3)CF_2CF_3$ | H | $CH_3$ |
| 6-19 | $SO_2CF_3$ | I | $CH_2CF_3$ | $CH_3$ | $CF(CF_3)CF_2CF_3$ | H | $CH_3$ |
| 6-20 | $SO_2CF_3$ | I | $CH_2CH_3$ | $CH_3$ | $CF(CF_3)CF_2CF_3$ | H | $CH_3$ |

Specific examples of an animal parasite that can be exterminated by the composition for exterminating an animal parasite of the invention can include the following parasites, although the invention is not limited to the examples.

Examples of the ectoparasites include

Siphonaptera pests such as *Ctenocephalides felis*, *Ctenocephalides canis*, *Xenopsylla cheopis*, *Echidnophaga gallinacea*, and *Pulex irritans*, pests in *Acari*, *Ixodidae* such as *Haemaphyxalislongicomis*, *Haemaphysalis japonica*, *Rhipicephalus sanguineus*, *Boophilus microplus*, *Dermacentor recticulatus*, *Dermacentor taiwanensis*, *Haemaphysalis flava*, *Ixodes ovatus*, *Ixodes persulcatus*, *Amblyomma americanum*, *Amblyomma maculatum*, *Dermacentor andersoni*, *Dermacentor occidentalis*, *Dermacentor variabilis*, *Haemaphysalis campanulata*, *Haemaphysalis megaspinosa*, *Ixodes nipponensis*, *Ixodes pacifcus*, *Ixodes ricinus*, and *Ixodes scapularis*, dipterous pests such as *Musca hervei*, *Musca bezzii*, *Haematobia irritans*, *Simulium iwatens*, *Culicoides oxystoma*, *Tabanus chrysurus*, *Culex pipiens*, and *Aedes albopictus*, and Phthiraptera pests such as *Haematopinus eurystemus and Damalinia ovis*.

Examples of the endoparasites include

Protozoa such as Rhizopoda including *Entamoeba histolytica*, Mastigophora including *Leishmania* and *Trichomonas*, Sporozoea including *Plasmodium* and *Toxoplasma*, and Ciliophora including *Balantidium coli*, helminths such as Nematoda including *Ascaris lumbricoides* and *Ancylostoma*, Acannthocephala including *Macracanthorhynchus hirudinaceus*, Nematomorpha including *Paragordius tricuspidatus*, Trematoda including *Clonorchis sinensis*, and Cestoda including *Taenia saginata*, nematodes such as *Ascaris*, *Toxocara*, *Toxascaris*, *Parascaris*, *Ascaridia*, *Heterakis*, Oxyuris, Capillaria, *Trichinella*, *Strongylus*, *Triodontophorus*, *Trichonema*, *Stephanurus*, *Desophagostomum*, *Chabertia*, *Syngamus*, *Ancylostoma*, *Uncinaria*, *Necator*, *Bunostomum*, *Trichostrongylus*, *Cooperia*, *Nematodirus*, *Haemonchus*, *Ostertagia*, *Dictyocaulus*, *Metastrongylus*, *Dirofilaria*, *Parafilaria*, *Setaria*, *Onchocerca*, *Habronema*, *Arduenna*, and *Acuaria*, cestodes such as *Diphyllobothrium*, *Anoplocephara*, *Moniezia*, *Dipylidium*, *Taenia*, *Dithyridium*, *Raillietina*, and *Echinococcus*, and flukes such as *Schistosoma*, *Paramphistomum*, and *Fasciola*.

In the invention, the animal parasite is preferably an ectoparasite, from the viewpoint of the parasiticidal activity, and the parasite is preferably at least one of Siphonaptera pests (particularly preferably *Ctenocephalides felis*) and Acarina pests (particularly preferably *Haemaphyxalislongicornis*, *Rhipicephalus sanguineus*, and *Boophilus microplus*).

Examples of the animals to which the composition for exterminating an animal parasite of the invention can be applied include domestic animals such as horses, cows, pigs, sheep, goats, rabbits, camels, buffalos, deer, minks, and chinchillas, fowls such as chickens, ducks, geese, and turkeys, pets such as dogs, cats, small birds, and monkeys, and laboratory animals such as rats, mice, golden hamsters, and guinea pigs, although the invention is not limited to the examples. Preferably, the animals exclude humans.

The composition for exterminating an animal parasite of the invention can be used as a parasiticide by any of the methods that are normally used, with no particular restriction.

In particular, for example, the composition may be dissolved, suspended, mixed, impregnated, adsorbed, or adhered on suitable solid and/or liquid carriers according to a formulation that is generally used, and, if necessary, together with an adjuvant and/or the like in a suitable proportion. And the composition may be prepared into an appropriate form in accordance with the intended use.

The solid or liquid carriers for use in the invention may be those normally used in agents for animals. From the viewpoint of easiness of treatment on the target animals, it is preferable to use a liquid carrier. Examples of the liquid carriers can include, for example, alcohols such as methyl alcohol, ethyl alcohol, isopropyl alcohol, tertiary butyl alcohol, and benzyl alcohol; propylene carbonate; N-methyl-2-pyrrolidone; and water. As the adjuvant, a surfactant, an antioxidant, an emulsifier, and the like can be used. Examples of the adjuvant can include, for example, surfactants such as polyoxyethylene alkylaryl ethers, polyoxyethylene sorbitan monolaurate, alkyl allyl sorbitan monolaurates, alkylbenzenesulfonates, alkylnaphthalene sulfonic acids, ligninsulfonic acid salts fatty alcohol sulfates, glycol monoalkyl ethers, and glycols; emulsifiers such as sorbitan monooleate, sorbitan monolaurate, caprylic acid monoglyceride, capric acid monoglyceride, isostearic acid monoglyceride, and propylene glycol monocaprylate; and antioxidants such as BHA and BHT.

The composition for exterminating an animal parasite of the invention may be administered orally or parenterally to an animal.

In a case in which the composition for exterminating an animal parasite of the invention is administered orally, the composition may be in the form of a capsule, a tablet, a pill, particles, granules, fine granules, a powder, a syrups, an enteric agent, a suspension, a paste, or a beverage or feed mixed with the drug.

In a case in which the composition for exterminating an animal parasite of the invention is administered parenterally, the composition may be in the form of an injectable, a drip, a suppository, an emulsion, a suspension, a drop, an ointment, a cream, a solution, a lotion, a spray, an aerosol, a cataplasm, or a tape.

Examples of methods for administration include the spot-on method in which a drop is dropped on the skin of the back shoulder region and the like of a target animal to exterminate an ectoparasite; local methods such as the pour-on method in which a liquid agent is applied along the back center line of a target animal to allow the applied agent to diffuse on the body surface, resulting in control of an ectoparasite; the methods in which an agent is released from a collar or the like that contains an agent; the methods in which a liquid agent, an ointment, or the like is directly applied to the body surface; the methods in which an aerosol or the like is applied with a spray or the like; the methods in which an injectable is injected intramuscularly, subcutaneously, or the like; and rectal administration with a suppository.

In addition to extermination of an endoparasite and an ectoparasite, the composition for exterminating an animal parasite of the invention can also prophylactically prevent a parasitic infections by applying the composition to the environments that are to be the infection routes. For example, the composition can prevent soil-borne infections from soils of upland fields and parks; percutaneous infections from aqueous systems such as river, lake, wetland, and paddy fields; oral infections from excrements of animals such as dogs and cats; oral infections from raw meats of sea water fish, fresh water fish, Crustacea, shellfish, domestic animals, and the like; and infections from, for example, mosquitoes, horseflies, flies, cockroaches, ticks, fleas, lice, assassin bugs, and chiggers.

In a case in which the composition for exterminating an animal parasite of the invention is used to exterminate parasites in the animals that are mammals or birds, the optimal dosage varies whether the composition is used for therapeutic purposes or for preventive purposes, and also varies with the type of infected parasites, the type and extent of infections, the dosage form, and the like. Generally, in the case of oral administration, the dosage is in the range from about 0.0001 mg to 10,000 mg per kilogram of body weight per day. In the case of parenteral administration, the dosage is in the range from about 0.0001 mg to 10,000 mg per kilogram of body weight per day. And the composition is administered in a single dose or divided doses.

The concentration of an active ingredient in the composition for exterminating an animal parasite of the invention is typically from 0.0001% to 100% by weight, preferably from 0.001% to 99% by weight, and more preferably from 0.005% to 80% by weight. In general, a parasiticide can be provided as a high-concentrated composition to be diluted to an appropriate concentration prior to use.

In addition to a 3-aminoxalylaminobenzamide derivative represented by Formula (1) according to the invention, the composition for exterminating an animal parasite of the invention can further include another insecticidal component that is generally known.

Examples of the another insecticidal component can include, for example, pyrethroid compounds such as permethrin, d-phenothrin, allethrin, pyrethrin, prallethrin, cyphenothrin, cyfluthrin, fenvalerate, fenpropathrin, transfluthrin, metofluthrin, resmethrin, cypermethrin, alpha-cypermethrin, bifenthrin, deltamethrin, lambda-cyhalothrin, d,d-trans-cyphenothrin, tetramethrin, and ethofenprox, organic phosphorus compounds such as dichlorvos, tetrachlorvinphos, fenthion, chlorpyrifos, chlorpyrifos methyl, malathion, pirimiphos methyl, fenitrothion, and diazinon, N-phenylpyrazole compounds such as fipronil, carbamate compounds such as propoxur, carbaryl, bendiocarb, metoxadiazone, and fenocarb, neonicotinoid compounds such as imidacloprid, clothianidin, thiamethoxam, acetamiprid, nitenpyram, and dinotefuran, diamide compounds such as chlorantraniliprole, cyantraniliprole, and fulvenediamide, insect growth regulators such as methoprene, pyriproxyfen, lufenuron, fenoxycarb, triflumuron, and chromafenozide, milbemycin oxime, milbemectin, lepimectin, abamectin, ivermectin, selamectin, spinosad, and rotenone.

The composition for exterminating an animal parasite of the invention include another insecticidal component as an active compound typically in an amount of from 0.02 parts by weight to 50 parts by weight and preferably from 0.1 parts by weight to 20 parts by weight, with respect to 1 part by weight of a 3-aminoxalylaminobenzamide derivative represented by Formula (1) according to the invention.

EXAMPLES

Exemplary examples of the 3-aminoxalylaminobenzamide derivatives according to the invention will be described with reference to the following Examples, although the invention is not limited to the examples.

Example 1

Compounds No. 1-132, 1-86, 1-154, 4-66, 5-15, 6-1, and 6-2, which are a 3-aminoxalylaminobenzamide derivative according to the invention, were produced.

Compound No. 1-132 was produced in accordance with the method described in Example 3 of WO 2012/020483.

Compound No. 1-86 was produced in accordance with the method described in Example 10 of WO 2010/090282.

Compound No. 1-154 was produced in accordance with the method described in Example 2 of WO 2012/020484.

Compound No. 4-66 was produced in accordance with the method described in Example 4 of WO 2012/020484.

Compound No. 5-15 was produced in accordance with the method described in Example 1 of WO 2012/164698.

Compounds No. 6-1 and 6-2 were produced by the method described below.

Example 1-1

Production of 2-fluoro-3-[N-(2-fluoroethyl)-N-methylaminoxalylamino]-N-[2-bromo-4-heptafluoroisopropyl-6-(trifluoromethyl)phenyl]benzamide (Compound No. 6-1)

0.22 g of N-(2,2,2-trifluoroethyl-N-methyloxalic acid, 0.55 g of 3-amino-2-fluoro-N-(2-bromo-4-(heptafluoroisopropyl)-6-(trifluoromethyl)phenyl)benzamide that was synthesized by the method described in WO 2010/018714, and 0.28 g of 2-chloro-1-methylpyridinium iodide were suspended in 10 ml of tetrahydrofuran. Then 0.33 g of triethylamine was added, and the mixture was stirred at room temperature overnight. Ethyl acetate and water were added to the reaction, and the layers were separated. The organic layer was sequentially washed with 10% aqueous hydrochloric acid, saturated sodium bicarbonate water, and saturated saline. The organic layer was dried over anhydrous sodium sulfate. Then the sodium sulfate was filtered, and the filtrate was concentrated under reduced pressure. The concentrated residue was purified by silica gel column chromatography (eluent: ethyl acetate:n-hexane=1:2) to obtain 0.43 g of the title compound as white solid.

$^1$H-NMR (CDCl$_3$, ppm) δ (9.67+9.54) (1H, s), 8.58-8.51 (1H, m), 8.21-8.15 (2H, m), 7.96-7.92 (2H, m), 7.40-7.36 (1H, m), (4.86+4.16) (2H, q), (3.65+3.23) (3H, s)

Example 1-2

Production of 2-fluoro-3-[N-(2-fluoroethyl)-N-methylaminoxalylamino]-N-[2-iodo-4-heptafluoroisopropyl-6-(trifluoromethyl)phenyl]benzamide (Compound No. 6-2)

0.11 g of N-(2,2,2-trifluoroethyl)-N-methyloxalic acid, 0.30 g of 3-amino-2-fluoro-N-(2-iodo-4-(heptafluoroisopropyl)-6-(trifluoromethyl)phenyl)benzamide that was synthesized by the method described in WO 2010/018714, and 0.14 g of 2-chloro-1-methylpyridinium iodide were suspended in 10 ml of tetrahydrofuran. Then 0.17 g of triethylamine was added, and the mixture was stirred at room temperature overnight. Ethyl acetate and water were added to the reaction, and the layers were separated. The organic layer was sequentially washed with 10% aqueous hydrochloric acid, saturated sodium bicarbonate water, and saturated saline. The layer was dried over anhydrous sodium sulfate. Then the sodium sulfate was filtered, and the filtrate was concentrated under reduced pressure. The concentrated residue was purified by silica gel column chromatography (eluent: ethyl acetate:n-hexane=1:2) to obtain 0.24 g of the title compound as white solid.

$^1$H-NMR (CDCl$_3$, ppm) δ (9.67+9.55) (1H, s), 8.58-8.52 (1H, m), 8.36 (1H, s), 8.24-8.22 (1H, m), 7.97-7.93 (2H, m), 7.39-7.36 (1H, m), (4.86+4.16) (2H, q), (3.69+3.23) (3H, s)

The following compounds were analyzed by LC-MS. The results are illustrated in Table 7 below.

TABLE 7

| Compound No. | MH$^+$ |
|---|---|
| 6-1 | 712 |
| 6-2 | 760 |
| 6-3 | 668 |
| 6-4 | 726 |
| 6-5 | 774 |
| 6-6 | 744 |
| 6-7 | 760 |
| 6-8 | 776 |
| 6-9 | 792 |
| 6-10 | 808 |
| 6-11 | 824 |
| 6-12 | 710 |
| 6-13 | 724 |
| 6-14 | 718 |
| 6-15 | 768 |
| 6-16 | 656 |
| 6-17 | 710 |
| 6-18 | 856 |
| 6-19 | 888 |
| 6-20 | 834 |

Now, exemplary formulations according to the invention will be described, although the invention is not limited to the examples. With regard to the formulation examples, "part" refers to "part by weight".

Formulation Example 1

Emulsion 10 parts of Compound No. 6-2, 6 parts of Sorpol 355S (surfactant from Toho Chemical Industry Co.), and 84 parts of Solvesso 150 (from Exxon Mobil Chemical Co.) were homogeneously mixed with stirring to obtain the composition for exterminating an animal parasite as emulsion.

Formulation Example 2

Ointment 1 part of Compound No. 1-86, 50 parts of white beeswax, and 49 parts of white petrolatum were thoroughly mixed to obtain the composition for exterminating an animal parasite as ointment.

Formulation Example 3

Tablet 2 parts of Compound No. 6-1, 10 parts of vegetable oil (olive oil), 3 parts of crystalline cellulose, 20 parts of white carbon, and 65 parts of kaolin were thoroughly mixed and then compressed to obtain the composition for exterminating an animal parasite as tablets.

Formulation Example 4

Injectable 10 parts of Compound No. 6-1, 10 parts of propylene glycol for a food additive, and 80 parts of vegetable oil (corn oil) were mixed to obtain the composition for exterminating an animal parasite as injectable.

Formulation Example 5

Solution 5 parts of Compound No. 1-132, 20 parts of surfactant, and 75 parts of ion-exchanged water were thoroughly mixed to obtain the composition for exterminating an animal parasite as a solution.

Next, the utility of the composition of the invention as a parasiticide will be specifically described with reference to the following test examples, although the invention is not limited to the examples.

Test Example 1

Insecticidal Test for *Ctenocephalides felis*

0.2 mL of an acetone solution was added dropwise to a round filter paper having a diameter of 4.0 cm that were grasped with tweezers so that each of the compounds was included in an amount of 50 μg/cm$^2$. After the addition, the filter paper was dried at room temperature for 24 hours for use in the test.

Three 200 mL vials were used per compound. The filter paper treated with a test agent was placed tightly into a lid of the vials so that fleas might be contacted with the paper.

About 20 emerged adult fleas were added to each of the 200 mL vials using an aspirator. Then immediately, the vial was sealed with the lid into which the filter paper that was treated with the agent was tightly placed. It was examined if the fleas that were already dead were added. In a case in which dead fleas were found, the number of the dead fleas was subtracted from the total number.

The vials were turned upside down so that the fleas were always contacted with the filter paper. After 24, 48, and 72 hours of the exposure, the conditions of the fleas were examined and classified into "alive" and "dead (including a moribund condition)" to determine the death rates (in triplicate). The death rates after 72 hours are illustrated in Table 8.

The death rates were calculated as follows:

Death Rate (%)=(Number of Dead Fleas including Moribund Fleas)/Total Number of Fleas×100

TABLE 8

| Active Ingredient (Compound No.) | Death Rate after 72 hours (%) |
|---|---|
| 1-132 | 100 |
| 1-154 | 85.2 |
| 5-15 | 80.0 |
| 6-1 | 100 |
| 6-2 | 100 |
| Untreated | 0 |

Test Example 2

Dry Film Insecticidal Test for *Haemaphyxalis Longicornis*

1 ml of an acetone solution that was prepared so that the compound was included at a concentration of 1 ppm was added dropwise to a glass petri dish having a diameter of 9 cm. After the addition, the acetone was air-dried for use in the test. About 10 young ticks were added. Then the dish was covered by a plastic film and sealed with a lid. The dish was placed in a constant temperature bath that was set at a temperature of 25° C., at a humidity of 100%, and with a light: dark cycle of 16:8.

After 48 hours of the exposure, the conditions of the ticks were examined and classified into "alive", "dead (including a moribund condition)", and "anguish". The death rates after 48 hours are illustrated in Table 9.

The death rates were calculated as follows:

Death Rate (%)=(Number of Dead and Anguish Ticks)/Total Number of Ticks×100

TABLE 9

| Active Ingredient (Compound No.) | Death Rate after 48 hours (%) |
|---|---|
| 1-86 | 100 |
| 1-132 | 100 |
| 1-154 | 100 |
| 4-66 | 100 |
| 5-15 | 100 |
| 6-1 | 100 |
| 6-2 | 100 |
| 6-3 | 100 |
| 6-4 | 100 |
| 6-5 | 100 |
| 6-6 | 100 |
| 6-7 | 100 |
| 6-8 | 100 |
| 6-9 | 100 |
| 6-10 | 100 |
| 6-11 | 100 |
| 6-12 | 100 |
| 6-13 | 100 |
| 6-14 | 100 |
| 6-15 | 100 |
| 6-16 | 100 |
| 6-17 | 100 |
| 6-18 | 100 |
| 6-19 | 100 |
| 6-20 | 100 |
| Untreated | 0 |

Data in Tables 8 and 9 confirm that the 3-aminoxalylaminobenzamide derivatives represented by Formula (1) according to the invention have excellent pesticidal effect against *Ctenocephalides felis* and *Haemaphyxalis longicornis*, which are an animal parasite.

The disclosure of Japanese Patent Application No. 2012-243601 filed on Nov. 5, 2012 is herein incorporated by reference in its entirety.

All publications, patent applications, and technical specifications described herein are herein incorporated by reference to the same extent as if the individual publication, patent application, and technical specification were specifically and individually indicated to be incorporated by reference.

The invention claimed is:

1. A composition for exterminating an animal parasite, the composition comprising, as an active ingredient, a 3-aminoxalylaminobenzamide derivative represented by the following Formula (1):

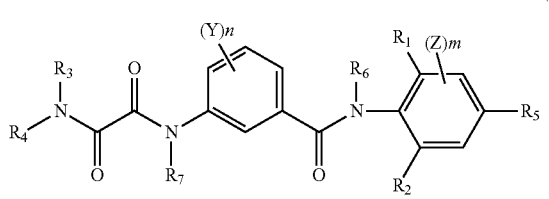

wherein, in Formula (1), $R_1$ represents a C1-C3 alkoxy group, a C1-C3 haloalkoxy group, a C1-C3 alkylthio group, a C1-C3 alkylsulfinyl group, a C1-C3 alkylsulfonyl group, a C1-C3 haloalkylthio group, a C1-C3 haloalkylsulfinyl group, a C1-C3 haloalkylsulfonyl group, a halogen atom, or a C1-C5 haloalkyl group, $R_2$ represents a hydrogen atom, a C1-C3 alkoxy group, a C1-C3 haloalkoxy group, a C1-C3 alkylthio group, a C1-C3 alkylsulfinyl group, a C1-C3 alkylsulfonyl group, a C1-C3 haloalkylthio group, a C1-C3 haloalkylsulfinyl group, a C1-C3 haloalkylsulfonyl group, a halogen atom, a C1-C5 haloalkyl group, or a C1-C5 alkyl group, when $R_1$ represents a halogen atom, $R_2$ represents a hydrogen atom, a C1-C3 alkylthio group, a C1-C3 alkylsulfinyl group, a C1-C3 alkylsulfonyl group, a C1-C3 haloalkylthio group, a C1-C3 haloalkylsulfinyl group, a C1-C3 haloalkylsulfonyl group, a halogen atom, or a C1-C5 haloalkyl group, when $R_2$ represents a halogen atom, $R_1$ represents a hydrogen atom, a C1-C3 alkylthio group, a C1-C3 alkylsulfinyl group, a C1-C3 alkylsulfonyl group, a C1-C3 haloalkylthio group, a C1-C3 haloalkylsulfinyl group, a C1-C3 haloalkylsulfonyl group, a halogen atom, or a C1-C5 haloalkyl group, each of $R_3$ and $R_4$ independently represents a hydrogen atom, a C1-C8 alkyl group, a C1-C8 haloalkyl group, a C2-C6 alkenyl group, a C2-C6 haloalkenyl group, a C2-C6 alkynyl group, a C3-C8 cycloalkyl group, or a C3-C8 halocycloalkyl group, or $R_3$ and $R_4$ together form a C3-C8 alkylene group, the C3-C8 alkylene group being optionally substituted by a halogen atom or a C1-C5 alkyl group, $R_5$ represents a C1-C5 haloalkyl group, each of $R_6$ and $R_7$ independently represents a hydrogen atom, a C1-C5 alkyl group, a C3-C8 cycloalkyl group, a C1-C5 haloalkyl group, a C1-C3 alkoxy-C1-C4 alkyl group, a C2-C6 alkenyl group, a C2-C6 haloalkenyl group, a C1-C4 alkylcarbonyl group, a C1-C4 haloalkylcarbonyl group, a C1-C4 alkylsulfonyl group, a C1-C4 haloalkylsulfonyl group, a C1-C3 alkoxycarbonyl group, or a C1-C3 haloalkoxycarbonyl group, each Y independently represents a hydrogen atom, a halogen atom, a hydroxyl group, a nitro group, a cyano group, a C1-C5 alkyl group, a C1-C5 haloalkyl group, a C1-C3 alkylamino group, a di-C1-C3 alkylamino group, a C1-C3 alkoxy group, or a C1-C3 haloalkoxy group, each Z independently represents a hydrogen atom, a halogen atom, a hydroxyl group, a nitro group, a cyano group, a C1-C5 alkyl group, a C1-C5 haloalkyl group, a C1-C3 alkoxy group, or a C1-C3 haloalkoxy group, and n represents an integer from 0 to 4, and m represents an integer from 0 to 2.

2. The composition for exterminating an animal parasite according to claim 1, wherein, in Formula (1), $R_1$ represents a methoxy group, a trifluoromethoxy group, a trifluoromethylthio group, a trifluoromethylsulfinyl group, a trifluoromethylsulfonyl group, a chlorine atom, a bromine atom, an iodine atom, a difluoromethoxy group, or a trifluoromethyl group; $R_2$ represents a chlorine atom, a bromine atom, an iodine atom, a methyl group, or an ethyl group; when $R_1$ represents a chlorine atom, a bromine atom, or an iodine atom, $R_2$ represents a chlorine atom, a bromine atom, or an iodine atom; when $R_2$ represents a chlorine atom, a bromine atom, or an iodine atom, $R_1$ represents a trifluoromethylthio group, a trifluoromethylsulfinyl group, a trifluoromethylsulfonyl group, a chlorine atom, a bromine atom, an iodine atom, a difluoromethoxy group, or a trifluoromethyl group; each of $R_3$ and $R_4$ independently represents a C1-C4 alkyl group, a C1-C4 haloalkyl group, a C3-C4 alkenyl group, a C3-C4 haloalkenyl group, a propargyl group, or a C3-C5 cycloalkyl group, or $R_3$ and $R_4$ together form a C4-C5 alkylene group that is optionally substituted by a methyl group; $R_5$ represents a C3-C4 haloalkyl group; $R_6$ and $R_7$ represent a hydrogen atom, Y represents a hydrogen atom or a halogen atom; and Z represents a hydrogen atom.

3. The composition for exterminating an animal parasite according to claim 2, wherein the compound represented by Formula (1) is represented by any one of the following Formulae (2) to (4) and (6):

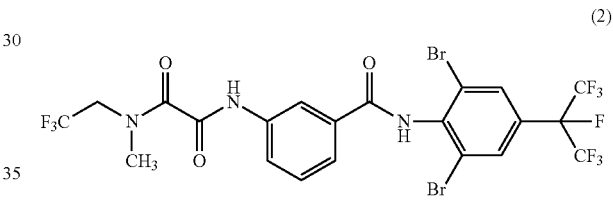

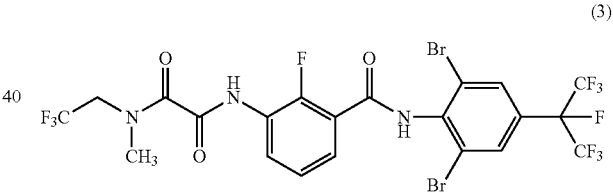

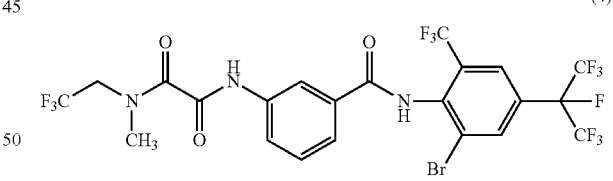

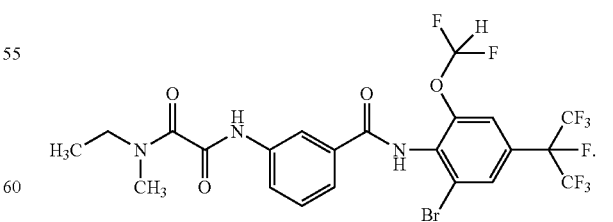

4. A composition for exterminating an animal parasite, the composition comprising, as an active ingredient, a 3-aminoxalylaminobenzamide derivative represented by the following Formula (1):

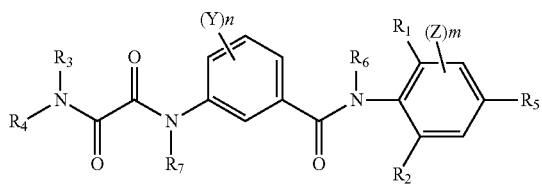

wherein, in Formula (1), $R_1$ represents a trifluoromethyl group, a difluoromethoxy group, a trifluoromethylthio group, a trifluoromethylsulfinyl group, or a trifluoromethylsulfonyl group;

$R_2$ represents a chlorine atom, a bromine atom, an iodine atom, a methyl group, or an ethyl group;

each of $R_3$ and $R_4$ independently represents a C1-C4 alkyl group or a C1-C4 haloalkyl group; $R_5$ represents a C3-C4 haloalkyl group; each of $R_6$ and $R_7$ independently represents a hydrogen atom or a C1-C5 alkyl group; Y represents a fluorine atom; and Z represents a hydrogen atom, and n represents an integer from 0 to 4, and m represents an integer from 0 to 2.

5. A composition for exterminating an animal parasite, the composition comprising, as an active ingredient, a 3-aminoxalylaminobenzamide derivative represented by the following Formula (1):

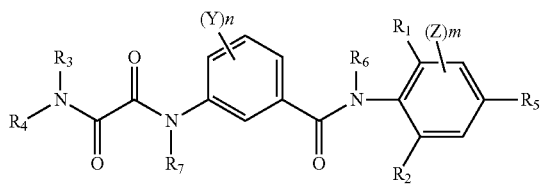

wherein, in Formula (1), each of $R_1$ and $R_2$ independently represents a hydrogen atom, a C1-C3 alkoxy group, a C1-C3 haloalkoxy group, a C1-C3 alkylthio group, a C1-C3 alkylsulfinyl group, a C1-C3 alkylsulfonyl group, a C1-C3 haloalkylthio group, a C1-C3 haloalkylsulfinyl group, a C1-C3 haloalkylsulfonyl group, a halogen atom, a C1-C5 haloalkyl group, or a C1-C5 alkyl group, each of $R_3$ and $R_4$ independently represents a hydrogen atom, a C1-C8 alkyl group, a C1-C8 haloalkyl group, a C2-C6 alkenyl group, a C2-C6 haloalkenyl group, a C2-C6 alkynyl group, a C3-C8 cycloalkyl group, or a C3-C8 halocycloalkyl group, or $R_3$ and $R_4$ together form a C3-C8 alkylene group, the C3-C8 alkylene group being optionally substituted by a halogen atom or a C1-C5 alkyl group, $R_5$ represents a C1-C5 haloalkyl group, each of $R_6$ and $R_7$ independently represents a hydrogen atom, a C1-C5 alkyl group, a C3-C8 cycloalkyl group, a C1-C5 haloalkyl group, a C1-C3 alkoxy-C1-C4 alkyl group, a C2-C6 alkenyl group, a C2-C6 haloalkenyl group, a C1-C4 alkylcarbonyl group, a C1-C4 haloalkylcarbonyl group, a C1-C4 alkylsulfonyl group, a C1-C4 haloalkylsulfonyl group, a C1-C3 alkoxycarbonyl group, or a C1-C3 haloalkoxycarbonyl group, each Y independently represents a hydrogen atom, a halogen atom, a hydroxyl group, a nitro group, a cyano group, a C1-C5 alkyl group, a C1-C5 haloalkyl group, a C1-C3 alkylamino group, a di-C1-C3 alkylamino group, a C1-C3 alkoxy group, or a C1-C3 haloalkoxy group, each Z independently represents a hydrogen atom, a halogen atom, a hydroxyl group, a nitro group, a cyano group, a C1-C5 alkyl group, a C1-C5 haloalkyl group, a C1-C3 alkoxy group, or a C1-C3 haloalkoxy group, and n represents an integer from 0 to 4, and m represents an integer from 0 to 2, wherein, in Formula (1), $R_1$ represents a methoxy group, a trifluoromethoxy group, a trifluoromethylthio group, a trifluoromethylsulfinyl group, a trifluoromethylsulfonyl group, a chlorine atom, a bromine atom, an iodine atom, a methyl group, an ethyl group, an isopropyl group, a difluoromethoxy group, or a trifluoromethyl group; $R_2$ represents a chlorine atom, a bromine atom, an iodine atom, a methyl group, or an ethyl group; each of $R_3$ and $R_4$ independently represents a C1-C4 alkyl group, a C1-C4 haloalkyl group, a C3-C4 alkenyl group, a C3-C4 haloalkenyl group, a propargyl group, or a C3-C5 cycloalkyl group, or $R_3$ and $R_4$ together form a C4-C5 alkylene group that is optionally substituted by a methyl group; $R_5$ represents a C3-C4 haloalkyl group; $R_6$ and $R_7$ represent a hydrogen atom, Y represents a hydrogen atom or a halogen atom; and Z represents a hydrogen atom, wherein, in Formula (1), $R_1$ represents a trifluoromethyl group, a difluoromethoxy group, a trifluoromethylthio group, a trifluoromethylsulfinyl group, or a trifluoromethylsulfonyl group;

$R_2$ represents a chlorine atom, a bromine atom, an iodine atom, a methyl group, or an ethyl group;

each of $R_3$ and $R_4$ independently represents a C1-C4 alkyl group or a C1-C4 haloalkyl group; $R_5$ represents a C3-C4 haloalkyl group; each of R6 and R7 independently represents a hydrogen atom or a C1-C5 alkyl group; Y represents a fluorine atom; and Z represents a hydrogen atom, and wherein the 3-aminoxalylaminobenzamide derivative represented by Formula (1) is represented by any one of the following Formulae (7) to (26):

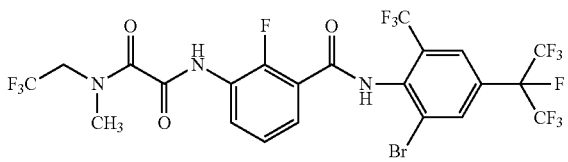

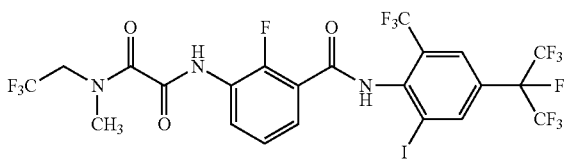

(9)
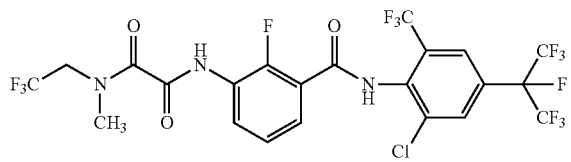
(10)
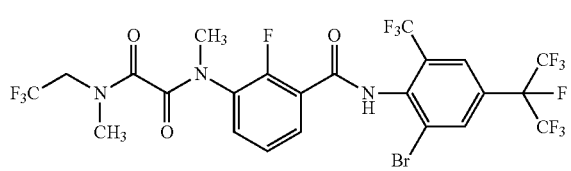
(11)
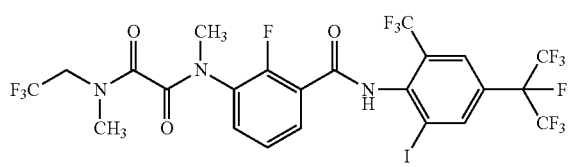
(12)
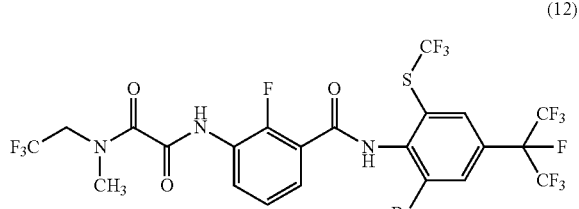
(13)
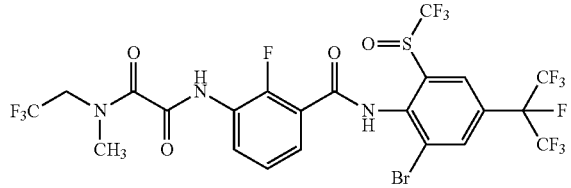
(14)
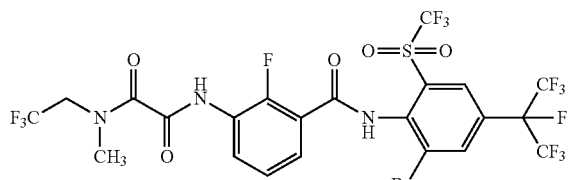
(15)
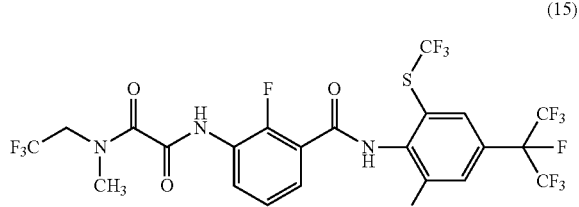
(16)
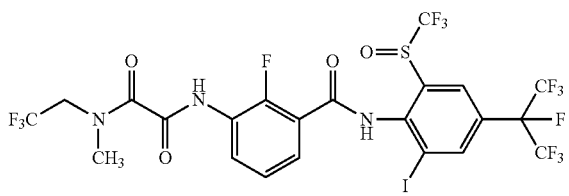
(17)
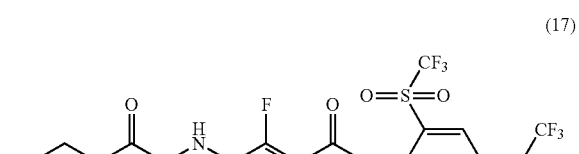
(18)
(19)
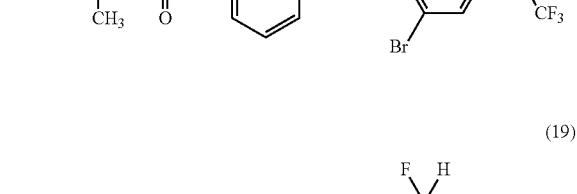
(20)
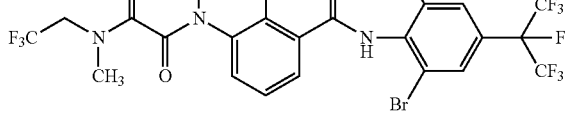
(21)
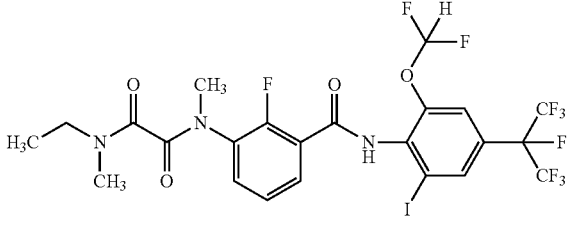
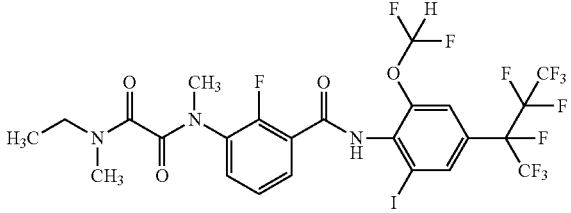

(22)

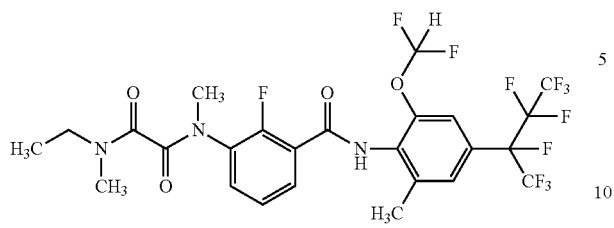

(23)

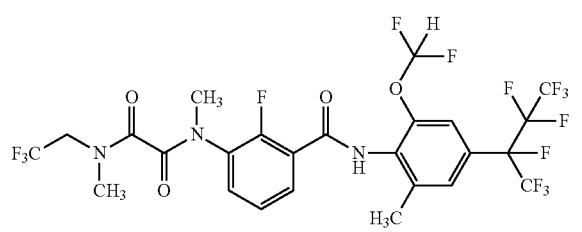

(24)

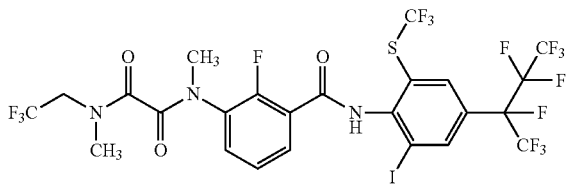

(25)

(26)

6. A method for exterminating an animal parasite, the method comprising administering, to an animal, the composition for exterminating an animal parasite according to claim 1.

7. The method for extermination according to claim 6, wherein the animal parasite is an ectoparasite.

8. The method for extermination according to claim 7, wherein the ectoparasite is a Siphonaptera pest.

9. The method for extermination according to claim 7, wherein the ectoparasite is an Acarina pest.

* * * * *